United States Patent [19]
Aoki et al.

[11] Patent Number: 4,872,901
[45] Date of Patent: Oct. 10, 1989

[54] HERBICIDAL PYRAZOLE SULFONYL IMINO-2H-1,2,4-THIADIAZOLO[2,3-A] PYRIMIDINES

[75] Inventors: Isao Aoki, Kawanishi; Takashi Kuragano, Takarazuka; Nobuyuki Okajima, Osaka; Yoshiyuki Okada, Suita, all of Japan

[73] Assignee: Takeda Chemical Industries, Ltd., Osaka, Japan

[21] Appl. No.: 921,420

[22] Filed: Oct. 22, 1986

[30] Foreign Application Priority Data

Oct. 25, 1985 [JP] Japan ................... 60-240258

[51] Int. Cl.$^4$ ................... A01N 43/90; C07D 497/22
[52] U.S. Cl. ................... 71/90; 544/255; 544/180; 544/219; 544/229; 544/311; 544/319
[58] Field of Search ................... 544/255, 254; 71/90, 71/99

[56] References Cited

U.S. PATENT DOCUMENTS

| 3,726,891 | 4/1973 | Pilgram | 544/255 |
| 3,769,287 | 10/1973 | Berger | 544/255 |
| 4,042,372 | 8/1977 | Harper | 71/90 |
| 4,353,920 | 10/1982 | Gay | 514/361 |
| 4,411,690 | 10/1983 | Tseng | 71/92 |
| 4,661,147 | 4/1987 | Dumas | 71/90 |
| 4,795,483 | 1/1989 | Gates | 71/90 |

FOREIGN PATENT DOCUMENTS 60-78980 5/1985 Japan .

Primary Examiner—Donald G. Daus
Attorney, Agent, or Firm—Wenderoth, Lind & Ponack

[57] ABSTRACT

Novel compounds of the formula:

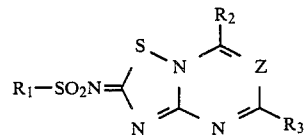

wherein $R_1$ is a pyrazolyl group which may be substituted; $R_2$ and $R_3$ respectively are a lower alkyl group or a lower alkoxy group; and Z is CH or N, which are useful as herbicides.

9 Claims, No Drawings

HERBICIDAL PYRAZOLE SULFONYL IMINO-2H-1,2,4-THIADIAZOLO[2,3-A9 PYRIMIDINES

The present invention relates to novel herbicidal compounds. More specifically the present invention relates to a compound of the formula:

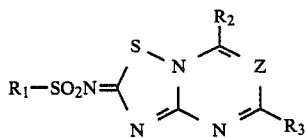
(I)

wherein $R_1$ is a pyrazolyl group which may be substituted; $R_2$ and $R_3$ respectively are a lower alkyl group or a lower alkoxy group, and Z is CH or N.

The compound (I) not only exhibits strong herbicidal activity on both paddy field weeds and field weeds, but also causes no phytotoxicity to crops, such as rice, wheat, barley, corn or soybean, thus working well as an excellent selective herbicide.

So far a wide variety of chemical agents have conventionally been used as herbicides. However, these are not satisfactory in herbicidal activity on weeds, phytotoxicity to crops, toxicity to mammals, fishes and shellfishes, and environmental pollution.

For example, among pyrazole compounds, the compounds of the formula

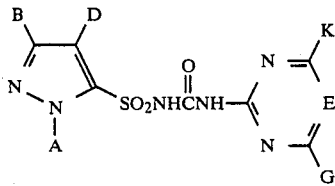

wherein A is hydrogen or a lower alkyl group etc.; B is hydrogen or a lower alkyl group; D is —COOQ (in which Q is a lower alkyl group etc.); K, G respectively are a lower alkyl or lower alkoxy group etc.; and E is nitrogen etc. have been known to show herbicidal activities (Japanese Published Unexamined Patent Application No. 78980/1985) From this publication, it was expected that compounds newly obtained by converting

group in the compounds of the formula into

group would show herbicidal activities not less than the compounds of the formula.

However it was proved by the present inventors that the thus obtained compounds do not show substantially excellent herbicidal activities.

The present inventors have conducted intensive research with regard to those compounds and found unexpectedly that novel compounds obtained by further subjecting the said compounds having

moiety to ring closure reaction have remarkable herbicidal activities.

The present inventors have made further studies based on these findings and thus brought the present invention to completion.

Referring to the formula (I), the pyrazolyl group represented by $R_1$ includes a pyrazol-3-yl group, a pyrazol-4-yl group and a pyrazol -5-yl group, preferably a pyrazol-5-yl group. These pyrazolyl groups may be substituted by suitable substituents at arbitrary positions, the number of the substituents being 1 to 3.

Examples of the substituents on these pyrazolyl groups include a lower alkyl group, a lower alkenyl group, a lower alkynyl group, a lower alkoxy group, a lower alkenyloxy group, an aryl group, an aryloxy group, an aralkyl group, an aralkyloxy group, an acyl group, an acyloxy group, carbamoyl, carbamoyloxy, sulfamoyl, halogen, a carboxyl group which may be esterified, nitro, cyano and a group of the formula:

wherein $R_4$ is an organic residue and n is an integer of 0, 1 or 2. In the above definitions, the lower alkyl group is preferably a straight-chain, branched or cyclic alkyl group of 1 to 6 carbon atoms, e.g. methyl, ethyl, n-propyl, isopropyl, n-butyl, isobutyl, sec-butyl, tert-butyl, n-pentyl, sec-pentyl, isopentyl, neopentyl, n-hexyl, isohexyl, cyclopropyl, cyclobutyl, cyclopentyl or cyclohexyl. The lower alkenyl group is preferably a straight-chain, branched or cyclic alkenyl group of 3 to 6 carbon atoms e.g. allyl, isopropenyl, 1-butenyl, 2-pentenyl, 2-hexenyl, cyclopropenyl, cyclobutenyl or cyclohexenyl. The lower alkynyl group is preferably a straight-chain or branched alkynyl group of 3 to 6 carbon atoms, e.g. propargyl, 2-butynyl, 3-butynyl, 3-pentynyl or 3-hexynyl. The lower alkoxy group is preferably a straight-chain or branched alkoxy group of 1 to 6 carbon atoms, e.g. methoxy, ethoxy, n-propoxy, isopropoxy, n-butoxy, isobutoxy, sec-butoxy, tert-butoxy, n-pentyloxy or n-hexyloxy. The alkenyloxy group is preferably a straight-chain, branched or cyclic alkenyloxy group of 3 to 6 carbon atoms e.g. allyloxy, 2-pentenyloxy, cyclohexenyloxy. The aryl group is preferably an aryl group of 6 to 12 carbon atoms, e.g. phenyl, naphthyl or biphenylyl. The aryloxy group is preferably an aryloxy group of 6 to 12 carbon atoms, e.g. phenoxy or naphthoxy. The aralkyl group is preferably an aralkyl group of 7 to 10 carbon atoms, e.g. benzyl, phenethyl or phenylpropyl. The aralkyloxy group is preferably an aralkyloxy group of 7 to 10 carbon atoms, e.g. benzyloxy, phenethyloxy, phenylpropyloxy. The acyl group is preferably an acyl group derived from an organic carboxylic acid, e.g. a lower alkylcarbonyl group, a lower alkenylcarbonyl group, an arylcarbonyl group, an aralkycarbonyl group (in these definitions, the lower alkyl group in the lower alkylcarbonyl group, the lower alkenyl group in the lower alkenylcarbonyl group, the aryl group in the arylcarbonyl group and the aralkyl group in the aralkylcarbonyl group have the same meaning as defined above) or a heterocyclic carbonyl group (in which the heterocyclic group is preferably a 5- or 6-membered heterocyclic group having at least one sulfur atom, one oxygen atom or one nitrogen atom, e.g. thienyl, benzothienyl, pyrrolyl, oxazolyl, piperazinyl, thiazolyl, thiadiazolyl, pyrazolyl, tetrazolyl or oxathiinyl.), and more concretely is acetyl, propionyl, butyryl, pentanoyl, hexanoyl, benzoyl, naphthoyl, benzylcarbonyl, phenethylcarbonyl, thienylcarbonyl or benzothienylcarbonyl. The acyloxy group is represented by a group of the formula: A—O—(wherein A is the acyl group as defined above), e.g. acetoxy, propionyloxy, butyryloxy, pentanoyloxy, hexanoyloxy, benzylcarbonyloxy, phenethylcarbonyloxy, benzoyloxy, naphthoyloxy, thienylcarbonyloxy or benzothienylcarbonyloxy. The halogen is fluorine, chlorine, bromine or iodine Examples of the organic residue represented by R₄ include a lower alkyl group, a lower alkenyl group, a lower alkoxy group, a lower alkenyloxy group, an aryl group, an aryloxy group, an aralkyl group, an aralkyloxy group, and a heterocyclic group, as mentioned above.

The lower alkyl group, the lower alkenyl group, the lower alkynyl group and the lower alkoxy group as mentioned above may be mono- to tri-substituted by a lower alkylthio group, such as a straight-chain or branched alkylthio group of 1 to 4 carbon atoms, e.g. methylthio, ethylthio, n-propylthio or isobutylthio, halogen, e.g. fluorine, chlorine, bromine or iodine, an alkoxy group, such as a straight-chain or branched alkoxy group of 1 to 6 carbon atoms, e.g. methoxy, ethoxy, n-propoxy, tert-butoxy or n-hexyloxy or/and a nitro group.

The aryl group, the aralkyl group, the aralkyloxy group and the aryloxy group, as mentioned above may be mono- to tri-substituted by a lower alkyl group, a lower alkenyl group, a lower alkynyl group, a lower alkoxy group, an acyl group, an acyloxy group, nitro, cyano, halogen, an acylamino group or/and a lower alkylthio group. In these definitions, the lower alkyl group, the lower alkenyl group, the lower alkynyl group, the lower alkoxy group, the acyl group, the acyloxy group, the halogen, and the lower alkylthio group have the same meaning as defined above. The acylamino group is an amino group which is mono- or di-substituted by the acyl group as mentioned above.

The carbamoyl, the carbamoyloxy and the sulfamoyl as mentioned above may be mono- or di-substituted by a lower alkyl group, a lower alkoxy group, an aryl group or/and an aralkyl group. In these definitions, the lower alkyl group, the lower alkoxy group, the aryl group and the aralkyl group have the same meaning as defined above.

The carboxyl group which may be esterified as mentioned above is a carboxyl group which may be esterified by the group, such as the above-mentioned lower alkyl group, lower alkenyl group, lower alkynyl group, aryl group, aralkyl group, acyl group or heterocyclic group.

Among these, preferable one is a compound of the formula:

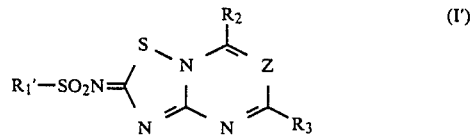

(I')

wherein R₁' is a pyrazolyl group which may be mono- to tri-substituted by a lower alkyl group, a lower alkenyl group, a lower alkynyl group, a lower alkoxy group, an aryl group, an aralkyl group, an aralkyloxy group, a carbamoyl group which may be mono- or di-substituted by a lower alkyl group, halogen, an optionally esterified carboxyl group, nitro, cyano or/and a group of the formula:

wherein R₄, is a lower alkyl group; and n is 0, 1 or 2; and other symbols have the same meaning as defined above.

In the definitions of R₁', the lower alkyl group and the lower alkyl group in the carbamoyl group which is mono- or di-substituted by a lower group is preferably a straight-chain, branched or cyclic alkyl group of 1 to 6 carbon atoms, e.g. methyl, ethyl, n-propyl, isopropyl, n-butyl, isobutyl, sec-butyl, tert-butyl, n-pentyl, sec-pentyl isopentyl, neopentyl, n-hexyl, isohexyl, cyclopropyl, cyclobutyl, cyclopentyl or cyclohexyl; and the lower alkenyl group is preferably a straight-chain or branched alkenyl group of 3 to 6 carbon atoms e.g. allyl, isopropenyl, 1-butenyl, 2-pentenyl or 2-hexenyl; and the lower alkynyl group is preferably a straight-chain or branched alkynyl group of 3 to 6 carbon atoms, e.g. propargyl, 2-butynyl, 3-butynyl, 3-pentynyl or 3-hexynyl; and the lower alkoxy group is preferably a straight-chain or branched alkoxy group of 1 to 6 carbon atoms, e.g. methoxy, ethoxy, n-propoxy, isopropoxy, n-butoxy, isobutoxy, sec-butoxy, tert-butoxy, n-pentyloxy or n-hexyloxy; and the aryl group is preferably an aryl group of 6 to 12 carbon atoms, e.g. phenyl, naphthyl or biphenylyl; and the aralkyl group is preferably an aralkyl group of 7 to 10 carbon atoms, e.g. benzyl, phenethyl or phenylpropyl; and the aralkyloxy group is preferably an aralkyloxy group of 7 to 10 carbon atoms, e.g. benzyloxy, phenethyloxy or phenylpropyloxy; and the halogen is fluorine, chlorine, bromine or iodine; and the optionally esterified carboxyl group is a carboxyl group which may be esterified by the above-mentioned lower alkyl group, lower alkenyl group, lower alkynyl group, aryl group or aralkyl group.

Examples of the carbamoyl group which is mono- or di-substituted by a lower group include, among others, N-methylcarbamoyl, N-ethylcarbamoyl, N,N-dimethylcarbamoyl, N,N-diethylcarbamoyl and N-methyl-N-propylcarbamoyl.

Examples of the esterified carboxyl group include, among others, methoxycarbonyl, ethoxycarbonyl, n-propoxycarbonyl, isopropylcarbonyl, n-butoxylcarbonyl isobutoxycarbonyl, t-butoxylcarbonyl, phenoxycarbonyl, naphthyloxycarbonyl, benzyloxylcarbonyl, benzhydryloxycarbonyl and trityloxycarbonyl.

The lower alkyl group represented by R₄, have the same meaning as defined for R₁'.

Examples of the group of the formula:

include, among others, methylthio, ethylthio, n-propylthio, t-buthylthio, methylsulfinyl, ethylsulfinyl, isopropylsulfinyl, methylsulfonyl, ethylsulfonyl, n-propylsulfonyl and n-hexylsulfonyl.

More preferably, $R_1$ is a pyrazol-5-yl group which may be mono- to tri-substituted by a lower alkyl group, a carbamoyl group which may be mono- or di-substituted by a lower alkyl group, an optionally esterified carboxyl group or/and halogen. Most preferably $R_1$ is a pyrazol-5-yl group of the formula:

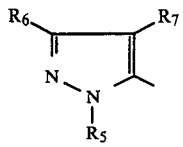

wherein $R_5$ is a lower alkyl group; $R_6$ is hydrogen or a lower alkyl group; and $R_7$ is an optionally esterified carboxyl group, halogen or a carbamoyl group which may be mono- or di-substituted by a lower alkyl group.

In these definitions, the lower alkyl group represented by $R_5$ or $R_6$, the optionally esterified carboxyl group, the lower alkyl group in the carbamoyl group which may be mono- or di-substituted by a lower alkyl group and the halogen represented by $R_7$ have the same meaning as defined in $R_1$.

Of these, desirably $R_5$ is methyl; $R_6$ is hydrogen or methyl; and $R_7$ is carboxyl esterified by an alkyl group of 1 to 4 carbon atoms, such as methyl, ethyl, n-propyl, isopropyl, n-butyl or tert-butyl, dimethylcarbamoyl or halogen. More desirably, $R_5$ is methyl, $R_6$ is hydrogen or methyl, and $R_7$ is methoxycarbonyl or ethoxycarbonyl.

The lower alkyl group represented by $R_2$ or $R_3$ is a straight-chain, branched or cyclic alkyl group of 1 to 6 carbon atoms, e.g. methyl, ethyl, n-propyl, isopropyl, n-butyl, isobutyl, sec-butyl, tert-butyl, n-pentyl, sec-pentyl, isopentyl, neopentyl, n-hexyl, isohexyl, cyclopropyl, cyclobutyl, cyclopentyl or cyclohexyl. The lower alkoxy group represented by $R_2$ or $R_3$ is a straight-chain or branched alkoxy group of 1 to 6 carbon atoms, e.g. methoxy, ethoxy, n-propoxy, isopropoxy, n-butoxy, isobutoxy, sec-butoxy, tertbutoxy, n-pentyloxy or n-hexyloxy.

Preferably, $R_2$ and $R_3$ respectively are an alkyl group of 1 to 4 carbon atoms, such as methyl, ethyl, n-propyl, isopropyl, n-butyl or tert-butyl, or an alkoxy group of 1 to 4 carbon atoms, such as methoxy, ethoxy, n-propoxy, isopropoxy, n-propoxy or tertpropoxy. Most preferably, $R_2$ and $R_3$ respectively are methyl or methoxy. Of these, desirably $R_2$ is methyl or methoxy and R is methoxy.

When the compound (I) contains an acid group e.g. a caboxylgroup, it may form a salt with a base, such as sodium, potassium or aluminum.

The compound (I) not only exhibits excellent herbicidal activity at an extremely low application rate on a wide range of weeds including both paddy field weeds, such as *Echinochloa oryzicola, Cyperus difformis, Scirpus juncoides, Monochoria vaginalis, Sagittaria pygmaea, Eleocharis acicularis, Cyperus serotinus, Eleocharis kuroguwai, Alisma canaliculatum, Sagittaria trifolia, Scirpus wallichii, Lindernia procumbens, Rotala indica, Potamogeton distinctus, Ludwiga prostrata or Flatine triandra,* and field weeds, such as *Digitaria adscendens, Setaria viridis, Amaranthus viridis, Abutilon theophrasti, Chenopodium album, Polygonum longisetum, Portulaca oleracea, Sida spinosa, Datura stramonium, Ipomoea purpurea, Xanthium strumarium, Echinochloa crus-galli, Panicum dichotomiflorum, Sorghum halepense, Cyperus rotundus, Avena fatua, Alopecurus myosuroides, Bromus tectorum, Stellaria media, Brassica Sp., Cassia obtusifolia, Matricaria chamomilla or Commelina communis,* but also induces no phytotoxicity to crops, such as rice, wheat, barley, corn or soybean, thus being highly safe for these crops.

The compound (I) exhibits highly selective herbicidal effect on various weeds as mentioned above, possesses no toxicity to mammals, fishes and shellfishes, and causes no environmental pollution, thus working well as a highly safe herbicide for paddyfields, fields, and non-cultivated land.

In utilizing the compound (I) as a herbicide, the compound (I) may take any of the known application formulation of agricultural chemicals. Thus, for example one or not less than two kinds of the compound (I), depending upon the application purpose, are dissolved, or suspended, in a suitable liquid carrier (for example, solvent) or mixed with, or adsorbed on, a suitable solid carrier to prepare emulsifiable concentrates, oil solutions, spray, wettable powders, dusts, DL(driftless)-dusts, granules, fine granules, fine granules F and tablets. If necessary, emulsifiers, suspension aids, spreading agents, penetrating agents, wetting agents, thickeners, stabilizers, etc. may also be incorporated in such compositions. These preparations can be produced by known manufacturing methods per se.

Suitable examples of the liquid carrier (solvent) which are used in the herbicides include solvents, such as water, alcohols (e.g. methyl alcohol, ethyl alcohol, n-propyl alcohol, isopropyl alcohol, or ethylene glycol), ketones (e.g. acetone or methyl ethyl ketone), ethers (e.g. dioxane, tetrahydrofuran, ethylene glycol monomethyl ether, diethylene glycol monomethyl ether or propylene glycol monomethyl ether), aliphatic hydrocarbons (e.g. kerosine, kerosene, fuel oil or machine oil), aromatic hydrocarbons (e.g. benzene, toluene, xylene, solvent naphtha or methylnaphthalene), halogenated hydrocarbons (e.g. dichloromethane, chloroform or carbon tetrachloride), acid amides (e.g. dimethylformamide or dimethylacetamide), esters (e.g. ethyl acetate, butyl acetate or glycerine esters of fatty acids) or nitriles (e.g. acetonitrile or propionitrile). These liquid carriers (solvents) may be used alone or as a mixture of two or more species in an appropriate ratio.

Examples of the solid carrier (diluent, dust-diluent) include vegetable powders (e.g. soybean powder, tobacco powder, wheat flour or wood flour), mineral powders (e.g. clay, such as kaolin, bentonite or acid clay; talc, such as steatite powder, or agalmatolite powder; silicas, such as diatomaceous earth or mica powder); alumina; sulfur powder and activated carbon. These solid carries may be used alone or as a mixture of two or more species in an appropriate ratio.

The surfactants which may be used as said emulsifiers, spreading agents, penetrating agents or dispersing agents include nonionic or anionic surfactants, such as soap; polyoxyethylene alkylaryl ethers (e.g. Noigen EA 142 ® from Dai-ichi Kogyo Seiyaku K.K., Japan); polyoxyethylene aryl esters (e.g. Nornal ® from Toho Chemical K.K., Japan); alkylsulfates (e.g. Emal 10 ® and Emal 40 ® from Kao Soap K.K., Japan); alkyl sulfonates (e.g. Neogen ® and Neogen T ® from Dai-ichi Kogyo Seiyaku Co. and Neopelex ® from Kao Soap K.K.); polyethylene glycol ethers (e.g. Nonipol 85 ®, Nonipol 100 ®, Nonipol 160 ® from Sanyo Kasei K.K., Japan); or polyhydric alcohol esters (e.g. Tween 20 ® and Tween 80 ® from Kao Soap K.K.).

The concentration of the compound (I) in the herbicide may be in the range of about 10 to 90 weight % in the case of emulsifiable concentrates and wettable powders, about 0.1 to 10 weight % in the case of an oil solutions, dusts and DL(driftless)-dusts and about 0.05 to 10 weight % in the case of granules, fine granules F and fine granules. These concentrations may be modified according to the intended application. As for emulsifiable concentrates and wettable powders, they are applied after diluting (e.g. 100 to 100000-fold) at site using a diluent, such as water.

When the compound (I) is used as a herbicide, the herbicide may be applied so that about 0.05 to 50 g, preferably 0.1 to 5 g, of the active ingredient [the compound (I)]is spread per are for paddy field, and 0.05 to 20 g, preferably 0.1 to 5 g, per are for field, though the application rate differs with application site, application season, application methods, target weed type etc.

When the compound (I) is applied against paddy field weeds, it is preferably used as a pre-emergence soil treatment herbicide or a leaf-stem and soil treatment herbicide.

For example, the herbicide of the present invention can be applied safely because it causes no phytotoxicity to a rice-plant even when it is applied immediately, or 2 to 3 weeks, after the transplantation.

The present herbicide, if necessary, may be used in combination with other herbicides, plant growth regulators, fungicides (e.g. organochlorinous fungicides, organosulfur fungicides, azolic fungicides or antibiotics), insecticides (e.g. pyrethroid insecticides, organophosphate insecticides or carbamate insecticides), acaricides, nematocides, synergists, attractants, repellents, colorants or/and fertilizers.

The compound (I) is produced by per se known methods, e.g. the method described in the Journal of Heterocyclic Chemistry, Vol. 20, p. 1127 (1983). For example, the compound (I) is produced by subjecting compound of the formula:

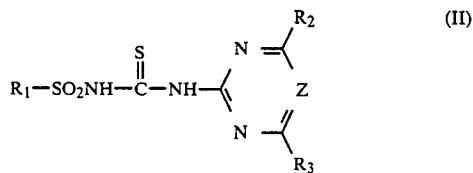 (II)

to a ring closure reaction.

The ring closure reaction is carried out by dehydrogenation reaction under oxidizing conditions.

This reaction is usually conducted by bringing the compound (II) into contact with an oxidizing agent. Examples of the oxidizing agent include halogenating agents, such as halogens (e.g. chlorine, bromine or iodine), N-halogenosuccinimides (e.g. N-chlorosuccinimide or N-bromosuccinimide), N-halogenoacetamides (e.g. N-chloroacetamide or N-bromoacetamide), N-halogenophthalimides (e.g. N-chlorophthalimide or N-bromophthalimide), chloramine T, or hypohalogenites (e.g. sodium hypochlorite, pottassium hypochlorite, calcium hypochlorite or sodium hypobromite); sulfonyl halides, such as arylsulfonyl halides (e.g. benzenesulfonyl chloride or p-toluenesulfonyl chloride), alkylsulfonyl halides (e.g. methanesulfonyl chloride or ethanesulfonyl chloride) or sulfuryl chloride; peroxy acids, such as hydrogen peroxide, performic acid, peracetic acid, peroxypropionic acid, perbenzoic acid, monoperoxyphthalic acid or trifluoroperoxyacetic acid; persulfates, such as sodium persulfate, potassium persulfate or ammonium persulfate; and metal-containing oxidizing agents, such as selenium dioxide, manganese dioxide, silver oxide, lead dioxide, mercuric oxide, ferric chloride, lead tetraacetate, potassium ferricyanide, permanganates or bichromates; nitric acid, oxygen and air.

In this ring-closure reaction, the oxidizing agent may be used in an amount which is necessary for completion of the reaction; theoretically, the oxidizing agent is may used so that active oxygen is generated in an amount of 0.5 mole per 1 mole of the compound (II). In cases where the oxydizing agent does not generate oxygen, the oxydizing agent may be used so that hydrogen is removed in an amount of 1 mole per 1 role of the compound (II). Usually use of an excess amount of the oxidizing agent causes a side reaction, and thus it is not preferable for excellent yield of the end product.

This reaction is carried out in a solvent which does not inhibit the reaction. As the solvent, use is made of a solvent inert to the reaction, such as water; alcohols, e.g. methanol, ethanol, n-propanol, isopropanol, n-butanol or tert-butanol; aromatic hydrocarbons, e.g. benzene, toluene, xylene, nitrobenzene or chlorobenzene; halogenated hydrocarbons, e.g. dichloromethane, chloroform or carbon tetrachloride; ethers, e.g. ethyl ether, dioxane, isopropyl ether or tetrahydrofuran (hereinafter referred to as THF); ketones, e.g. acetone or methyl ethyl ketone; nitriles, e.g. acetonitrile or propionitrile; amides, e.g. dimethylformamide (hereinafter referred to as DMF), dimethylacetamide (hereinafter referred to as DMAC) or hexamethylphosphoric triamide (hereinafter referred to as HMPA); esters, e.g. methyl acetate, ethyl acetate or butyl acetate; sulfoxides, e.g. dimethyl sulfoxide (hereinafter referred to as DMSO); aliphatic carboxylic acids, e.g. formic acid, acetic acid or propionic acid; or organic tertiary amines, e.g. pyridine, γ-collidine, quinoline, triethylamine, tri-n-propylamine or N,N-dimethylaniline. These solvents may be used alone or as a mixture of two or more species in an arbitrary ratio.

This ring-closure reaction may be conducted in the presence of a base so that the reaction proceeds smoothly. Examples of the base are inorganic bases, such as alkali metal hydroxides e.g. potassium hydroxide or sodium hydroxide, alkaline earth metal hydroxides e.g. calcium hydroxide, alkali metal bicarbonates e.g. potassium bicarbonate, alkali earth metal carbonates (e.g. calcium carbonate, or ammonia; and organic bases, such as organic tertiary amines, e.g. pyridine, collidine, quinoline, triethylamine, tri-n-propylamine, N,N-dimethylbenzylamine, N,N-dimethylaniline, 1,8-diazabicyclo[5.4.0]-7-undecene (hereinafter referred to as DBU), 1,4-diazabicyclo [2.2.2]octane (hereinafter referred to as DBO) or 1,5-diazabicyclo[4.3.0]non-5-ene (hereinafter referred to as DBN). The base may be used in an amount of about 0.5 to 3 moles per 1 mole of the compound (II).

Preferable examples of the oxidizing agent as mentioned above include halogenating agents, such as chlorine, bromine, iodine, N-chlorosuccinimide, N-bromosuccinimide, N-bromacetamide, N-bromophthalimide or chloramine T; and sulfonyl chlorides, such as sulfuryl chloride, benzenesulfonyl chloride, p-toluenesulfonyl chloride or methanesulfonyl chloride.

When this reaction is carried out in the presence of a base, the solubility of the compound (II) increases, thus not only making the reaction proceed more smoothly but also reducing the production of by-products.

The compound (II) as the starting material may isomerize in the presence of a base and may exist in the form of the compound of the formula:

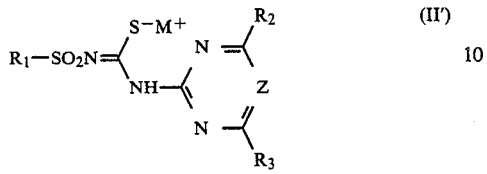

(II')

wherein $R_1$, $R_2$, $R_3$ and Z have the same meaning as defined above; $M^+$ is an alkali metal ion, $\frac{1}{2}X^{++}$, (wherein X is an alkaline earth metal) or an ammonium ion.

Referring to the above formula, the examples of the alkali metal in the alkali metal ion represented by $M^+$ include lithium, sodium and potassium. The examples of the alkaline earth metal represented by X in $\frac{1}{2}X^{++}$, include magnesium, calcium and barium. The examples of the ammonium ion include the organic tertiary amines which are protonated. After the compound (II') is separated according to per se known methods, it may be used as a starting material for this ring closure reaction.

The reaction temperature may be chosen in a range of about $-60°$ C. to about $100°$ C., but is usually about $-20°$ C. to about $50°$ C. The reaction time is a relatively short period, i.e. about 5 minutes to about 2 hours. The reaction almost goes to completion simultaneously with the completion of the addition of the oxidizing agent in many cases.

The end-point of the reaction can be easily recognized by thin-layer chromatography, high performance liquid chromatography, etc. When the compound (I) obtained in the above-described manner contains a free carboxylic acid, it can be converted to a salt with a base by the conventional procedure. The salt may for example be the salt with sodium, potassium, aluminum or calcium, for instance. When the compound (I) is obtained in the form of carboxylic acid salt it can be converted to a free carboxylic acid by the conventional procedure. The compound (I) can be separated and purified by per se known methods, e.g. concentration, concentration under reduced pressure, distillation under reduced pressure, solvent transformation, solvent extraction, crystallization, recrystallization or/and chromatography.

The compound (II) is used as the starting material for producing the compound (I). Moreover, the compound (II) itself exhibits herbicidal activity on paddy field and field weeds, working as a selective herbicide for crops, such as rice or wheat, although the herbicidal activity is not strong enough.

The compound (II) may be produced by any of the following production methods 1 to 3.

Production method 1

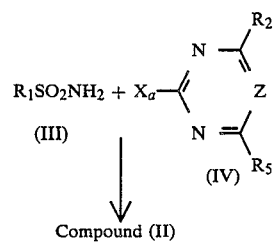

In the above formulas $R_1$, $R_2$, $R_3$ and Z have the same meaning as defined above, and $X_a$ is an isothiocyanato group or a mono- or bis-(phenoxythiocarbonyl)amino group.

In this reaction, the compound (IV) is used in an amount of about 0.8 to about 3 moles, preferably about 0.9 to about 1.3 moles per 1 mole of the compound (III).

This reaction is conducted in a solvent inert to the reaction. Examples of the solvent include aromatic hydrocarbons, such as benzene, toluene or xylene; halogenated hydrocarbons, such as dichloromethane, chloroform or carbon tetrachloride; ethers, such as ethyl ether, isopropyl ether, dioxane or THF: nitriles, such as acetonitrile or propionitrile; esters, such as ethyl acetate; hydrocarbons such as petroleum ether, petroleum benzin or hexane; and ketones, such as acetone or methyl ethyl ketone. These solvents may be used alone or as a mixture of two or more species.

This reaction may be carried out in the presence of a base. Suitable bases are organic bases, such as tri-alkyl substituted amines, the alkyl having 1 to 6 carbon atoms (e.g. trimethylamine or triethylamine), or tertiary amines (e.g. pyridine, Y-collidine, DBU, DBO or DBN); and inorganic bases, such as alkali metal hydroxides (e.g. potassium hydroxide or sodium hydroxide), alkaline earth metal hydroxides (e.g. calcium hydroxide), alkali metal carbonates (e.g. potassium carbonate or sodium carbonate), alkali metal bicarbonates (e.g. potassium bicarbonate or sodium bicarbonate), or alkaline earth metal carbonates (e.g. calcium carbonate).

The base may be used in an amount of about 0.8 to about 1.2 moles per 1 mole of the compound (IV).

The reaction temperature may be chosen in a range of from about $0°$ C. to about $150°$ C. Preferably the reaction temperature is about $10°$ C. to about $60°$ C. The reaction goes to completion within a period of from about 30 minutes to about 10 hours. The end-point of the reaction can be recognized by thin-layer chromatography, high performance liquid chromatography, etc.

Production method 2

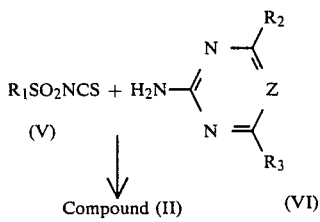

In the above formulas, $R_1$, $R_2$, $R_3$, and Z have the same meaning as defined above.

In this reaction the compound (V) is used in an amount of about 0.8 to about 3 moles, preferably about 0.9 to about 1.3 moles per 1 mole of the compound (VI).

This reaction is usually carried out in a solvent inert to the reaction. Examples of the solvent include aromatic hydrocarbons, such as benzene, toluene or xylene; halogenated hydrocarbons, such as dichloromethane, chloroform or carbon tetrachloride; ethers, such as ethyl ether, isopropyl ether, dioxane or THF; nitriles, such as acetonitrile or propionitrile; esters, such as ethyl acetate; hydrocarbons, such as petroleum ether, petroleum benzin or hexane; and ketones, such as acetone or methyl ethyl ketone. These solvents may be used alone or as a mixture thereof. This reaction may be carried out in the presence of a base. Examples of the base are organic bases, such as DBU, DBO, DBN, triethylamine, tri-n-propylamine or pyridine and inorganic bases, such as sodium amide or sodium hydride.

The base may be used in an amount of about 0.8 to about 1.2 moles perl mole of the compound (V).

The reaction temperature may be chosen in a range of from about 0° C. to about 150° C., but preferably is about 10° C. to about 100° C. The reaction goes to completion within a period of from about 30 minutes to about 10 hours. The end-point of the reaction can be recognized by thinlayer chromatography, high performance chromatography, etc.

Production method 3

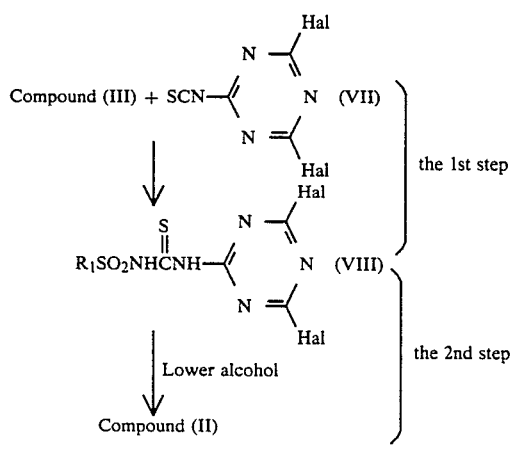

(In the compound (II), $R_1$ has the same meaning as defined above; Z is N, and $R_2$ and $R_3$ respectively are a lower alkoxy group.)

In the above formulas, $R_1$ has the same meaning as defined above; Hal is halogen, such as chlorine or bromine. The lower alkoxy group represented by $R_2$ or $R_3$, has the same meaning as defined for $R_1$.

The 1st step of the reaction is a process of producing the compound (VIII) by a reaction of the compound (III) with the compound (VII).

The compound (VII) is used in an amount of about 0.8 to about 2 moles per 1 mole of the compound (III).

This reaction is carried out in a solvent inert to the reaction.

Examples of the solvent include aromatic hydrocarbons, such as benzene, toluene or xylene; halogenated hydrocarbons, such as dichloromethane, chloroform or carbon tetrachloride; ethers, such as ethyl ether, isopropyl ether, dioxane or THF; nitriles, such as acetonitrile or propionitrile; esters such as ethyl acetate; and hydrocarbons, such as petroleum ether, petroleum benzin or hexane. These solvents may be used alone, or as a mixture thereof This reaction may be carried out in the presence of a base. Examples of the base are organic bases, such as trialkyl substituted amines, the alkyl having 1 to 6 carbon atoms, e.g. trimethylamine or triethylamine, or tertiary amines, e.g. as pyridine, γ-collidine, DBU, DBO or DBN; and inorganic bases, such as alkali metal hydroxides, e.g. potassium hydroxide or sodium hydroxide, alkaline earth metal hydroxides, e.g. calcium hydroxide, alkali metal carbonates, e.g. potassium carbonate or sodium carbonate, alkali metal bicarbonates, e.g. potassium bicarbonate or sodium bicarbonate, or alkaline earth metal carbonates, e.g. calcium carbonate.

The base may be used in an amount of about 0.8 to about 1.2 moles per 1 mole of the compound (VII).

The reaction temperature may be chosen in a range of from about 0° C. to about 100° C. The reaction time is about 1 hour to about 10 hours.

The thus obtained compound (VIII) may be subjected to the next reaction directory in the form of a reaction solution or after being separated and purified by conventional methods per se.

The 2nd step of the reaction is a process of producing the compound (II) wherein $R_1$ has the same meaning as defined above; $R_2$ and $R_3$ respectively are a lower alkoxy group by a reaction of the compound (VIII) with a lower alcohol.

In this reaction, as the lower alcohol use is made of alcohols of 1 to 6 carbon atoms, such as methanol, ethanol, n-propanol, tert-butanol or n-hexanol.

The lower alcohol may be used in an amount of about 2 to about 10 moles per 1 mole of the compound (VIII). In addition, it may be used in an large excess amount or as a solvent.

This reaction is carried out in a solvent inert to the reaction. Examples of the solvent include aromatic hydrocarbons, such as benzene, toluene or xylene; halogenated hydrocarbons, such as dichloromethane, chloroform or carbon tetrachloride; ethers, such as ethyl ether, dioxane or THF; ketones, such as acetone or methyl ethyl ketone; nitriles, such as acetonitrile or propionitrile; amides such as DMF, DMAC or HMPA; esters such as methyl acetate or ethyl acetate; and sulfoxides, such as DMSO. These solvents may be used alone or as a mixture thereof.

The reaction temperature is about room temperature (about 15° C.) to about 120° C. The reaction time is about 30 minutes to about 10 hours.

The compound (II) obtained can be separated and purified by per se known methods, e.g. concentration, concentration under reduced pressure, distillation under reduced pressure, pH adjustment solvent transformation, solvent extraction, crystallization, recrystallization or/and chromatography.

The pyrazolesulfonamide of the formula (III), which is the starting material in Production Methods 1 and 3 for the compound (II), can be produced by per se known methods or similar methods thereof. The compound (III) may be produced by the method shown below.

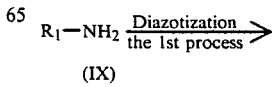

(IX)

-continued

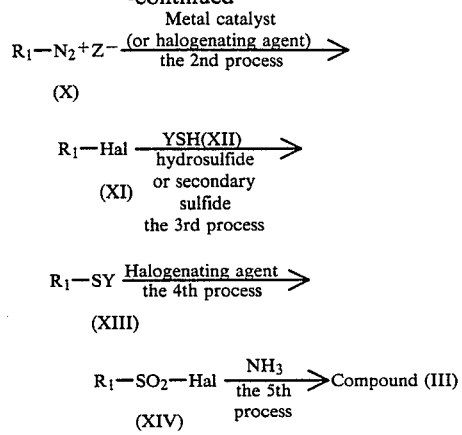

In the above formulas, $R_1$ and Hal have the same meaning as defined above; Y is hydrogen, a lower alkyl group or an aralkyl group; $Z^-$ is a halogenide ion or $\frac{1}{2}$ $SO_4{}^{--}$. The lower alkyl group and the aralkyl group represented by Y and the halogen in the halogenide ion represented by $Z^{31}$ have the same meaning as defined above.

The compound (XI) in the above scheme is an important intermediate compound for producing the compound (I). The inventors have studied to find a novel method by which this compound can be produced easily as well as with a high yield, and as a result, found that it can be produced with a high yield by diazotizing the compound (IX) (the 1st process) and then by converting the diazotized compound to the compound (XI) in the presence of a metal catalyst (the 2nd process) By this method for producing the compound (XI) the compound (XI) is obtained easily, with a high purity and high yield, thus being highly useful for industrial application.

The 1st process is a process for producing the compound (X) by subjecting the compound (IX) to diazotization.

This reaction is carried out by reacting the compound (IX) with a diazotizing reagent. Examples of the diazotizing reagent are alkali metal nitrites (e.g. sodium nitrite or potassium nitrite), nitrous acid esters (e.g. isoamyl nitrite or ethyl nitrite), nitrosylsulfuric acid, nitrous acid gas, etc. The diazotizing reagent is used in an amount of about 0.8 about 1.2 moles per 1 mole of the compound (IX).

This reaction is conducted in a solvent inert to the reaction. Examples of the solvent include water; organic aliphatic carboxylic acids, such as formic acid or acetic acid; inorganic acids, such as hydrochloric acid, hydrobromic acid, sulfuric acid or phosphoric acid; and alcohols, such as methanol, ethanol, n-propanol or isopropanol. These solvents may be used alone or as a mixture of two or more species.

This reaction is usually carried out under an acid condition. If necessary, an acid, such as inorganic acids e.g. sulfuric acid, hydrochloric acid or hydrobromic acid, may be added so that acid conditions is maintained. In such a case, the acid is usually used in an amount of about 1 to about 3 moles per 1 mole of the compound (IX), but the acid may be used in an extremely excess amount.

The reaction temperature is about $-20°$ C. to about $40°$ C., preferably about $-10°$ C. to about $5°$ C.

The reaction usually goes to completion within a period of from about 5 minutes to about 12 hours, though the reaction time also varies with the addition rate of the diazotizing agent.

The compound (X) obtained above may be subjected to the next process directly in the form of a solution or after being separated by per se known methods (e.g. crystallization).

The 2nd process is the process for converting the compound (X) to the compound (XI) in the presence of a metal catalyst.

When the compound (X) contains a halogenide ion for $Z^-$, the reaction is carried out by subjecting the compound (X) to decomposition reaction in the presence of a metal catalyst. Examples of the metal catalyst include transition metals, such as copper, cobalt or zinc, their halides (e.g. chlorides or bromides), their inorganic acid salts (e.g. sulfates or nitrates), their organic carboxylic acid salts (e.g. acetates), and their hydroxides. These metal catalysts may be used in an amount of about 0.01 to about 3 moles per 1 mole of the compound (X). When the compound (X) contains $\frac{1}{2}$ $SO_4{}^{--}$ for $Z^-$, the reaction is carried out by halogenating the compound (X) with a halogenating agent. As the halogenating agent, use is made of the metal halide mentioned above, such as copper chloride or copper bromide In such a case, the halogenating agent may be used in an amount of about 1 to about 3 moles per 1 mole of the compound (X). This reaction is usually carried out in a solvent inert to the reaction. Examples of the solvent include water; organic carboxylic acids, such as formic acid, acetic acid or propionic acid; inorganic acids, such as hydrochloric acid, hydrobromic acid or sulfuric acid; and alcohols, such as methanol, ethanol, n-propanol or isopropanol. These solvents may be used alone or as a mixture of two or more species.

This reaction is usually carried out under an acid condition. An inorganic acid, such as hydrochloric acid, hydrobromic acid, sulfuric acid or phosphoric acid; or an organic acid, such as formic acid, acetic acid or propionic acid is used to keep the acid condition of the reaction mixture. These acids may be used as solvents as well.

Preferably this reaction is carried out in the presence of sulfur dioxide. In this reaction, by addition of sulfur dioxide the compound (XI) can be produced at a high yield and at a high purity. Sulfur dioxide is used in an amount of about 0.3 to 3 moles per 1 mole of the compound (X), but it may be used in great excess.

Sulfur dioxide may be bubbled directly into the reaction mixture in the form of a gas. A compound which generates sulfur dioxide under an acid condition may be added to the compound (X) during the reaction. Examples of the compound which generates sulfur dioxide under an acid condition include alkali metal bisulfites (e.g. sodium bisulfite or potassium bisulfite), ammonium bisulfite, alkali metal sulfites (e.g. sodium sulfite or potassium sulfite), alkaline earth metal sulfites (e.g. calcium sulfite or barium sulfite) and ammonium sulfite.

The reaction temperature is about $-20°$ C. to about $100°$ C., preferably about $-5°$ C. to about $10°$ C. The reaction time is about 30 minutes to about 12 hours.

The 3rd process is a process for producing the compound (XIII) by reacting the compound (XI) with the compound (XII) or a hydrosulfide, or a secondary sulfide.

Of the compound (XII) preferred species are hydrogen sulfide, methyl mercaptan, ethyl mercaptan and benzyl mercaptan. Of the hydrosulfides preferred species are sodium hydrosulfide and potassium hydrosulfide. Of the secondary sulfides preferred species are sodium sulfide, potassium sulfide and ammonium sulfide.

The compound (XII), the hydrosulfide or the secondary sulfide is used in an amount of about 0.5 to about 3 moles, preferably about 0.9 to about 1.2 moles, per 1 mole of the compound (XI).

This reaction can usually be carried out smoothly in a solvent. Examples of the solvent include acetone, THF, ethyl acetate, dioxane, acetonitrile, chloroform, dichloromethane, DMF, DMAC and DMSO. These solvents may be used alone or as a mixture of two or more species in an appropriate ratio.

This reaction is usually conducted in the presence of a base. Examples of the base are alkali metal hydrides -(e.g sodium hydride or lithium hydride), sodium amide, alkalimetal bicarbonates (e.g. sodium bicarbonate or potassium bicarbonate, etc.), and alkali metal carbonates (e.g. sodium carbonate, or potassium carbonate). The base is used in an equimolar amount per the compound (XII).

The reaction temperature is not specially limited, but usually about 0° C. to about 60° C. The reaction time is about 30 minutes to about 3 hours.

When the compound (XIII) has an esterified carboxyl group as the substituent, the esterified carboxyl group may be converted to the free carboxyl group by a per se known hydrolysis process, and if necessary, the free carboxyl group may be esterified. The hydrolysis is carried out easily by using an alkali, such as sodium hydroxide or potassium hydroxide. The reaction is preferably conducted in the presence of the said alkali or its aqueous solution, in a solvent, such as water, methanol or ethanol. This reaction is conducted at a temperature range of room temperature (about 15° C.) to the boiling point of the solvent. The alkali is used in an amount of about 1 to about 6 moles, preferably about 3 to about 4 moles per 1 mole of the compound (XIII). The carboxylic acid produced by this method may be converted to an ester by esterification, if necessary. The esterification may be carried out by per se known methods. For example, diazomethane, combinations of an alcohol (e.g. methanol, ethanol, n-propanol, isopropanol, n-butanol or tert-butanol) and an acid (e.g. hydrogen chloride, sulfuric acid or p-toluenesulfonic acid), and a combination of thionyl chloride and the said alcohol are used in the esterification.

When the compound (XIII) has an esterified carboxyl or carboxyl group as the substituent, it can be converted to a carboxamide derivative by reaction of ammonia or an amine. Examples of the amine are methylamine, ethylamine, propylamine and dimethylamine, diethylamine. This conversion reaction is carried out by per se known methods, in which e.g. a combination of ammonia or an amine and a suitable binder, such as dicyclohexyl carbodiimide, diethylphosphoryl cyanide or 2-chloro-1methylpyridinium iodide, and a combination of ammonia or an amine and thionyl chloride are employed. When the compound (XIII) contains a carboxyl group as the substituent, the carboxyl group may be eliminated by decarboxylation reaction according to per se known methods.

The decarboxylation reaction is carried out in a solvent, e.g. water, ethanol, propanol or isopropanol in the presence of a mineral acid e.g. hydrochloric acid, hydrobromic acid or sulfuric acid. The reaction temperature is room temperature to the reflux temperature of the solvent employed. The reaction time is about 1 hour to about 24 hours.

When compound (XIII) has no substituent at the 3-, the 4-, or the 5- position of its pyrazole ring, it is feasible to substitute a hydrogen atom at the 3-, 4-, or 5- position with a halogen, a nitro group or an acyl group, according to a conventional halogenation, nitration or acylation reaction.

The 4th process is a process for producing the compound (XIV) by reacting the compound (XIII) with a halogenating agent.

Examples of the halogenating agent include halogens, such as chlorine, bromine or iodine; halogene halides, such as iodine chloride, iodine bromide or bromine chloride; hypohalogenous acids, such as hypochlorous acid, hypobromous acid or hypoiodous acid; and hypohalogenites of a metal, such as sodium, potassium, calcium, barium or copper (cuprous and cupric).

Of these reagents, halogens and halogen halides are used in the presence of an oxidizing agent such as oxygen or hydrogen peroxide, or in combination with water or acetic acid.

The reaction is usually carried out in a solvent. Examples of the solvent include water; alcohols, such as methanol, ethanol, isopropanol, n-butanol or tert-butanol; sulfolane; dioxane; THF; acetonitrile; acetone; chloroform; dichloromethane; carbon tetrachloride; benzene; toluene; and acetic acid. The reaction temperature is not specially limited, but is usually about 0° C. to about 70° C. The reaction may be conducted under cooling to about −80° C., or under heating to the reflux temperature of the solvent, depending on the type of the halogenating agent.

The reaction usually goes to completion within a period of from about 30 minutes to about 24 hours.

When the compound (XIII) is represented by a compound of the formula:

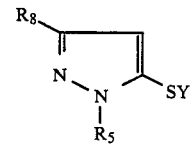

wherein the symbols have the same meaning as defined above, the 4-position of the pyrazole ring may also be halogenated simultaneously.

The 5th process is a process for producing the compound (III) by reacting the compound (XIV) with ammonia.

Ammonia is used in an amount of about 1 to about 100 moles, preferably about 2 to about 30 moles, per 1 mole of compound (XIV).

The reaction is usually carried out in a solvent. Examples of the solvent include polar solvents, such as water; alcohols, such as methanol, or butanol; dimethyl sulfide; DMF; DMAC; glymes, such as methyl cellosolve, dimethyl cellosolve or diethylene glycol dimethyl ether; dioxane; THF or acetonitrile, or their mixtures; and mixtures of these polar solvents and non-polar solvents, such as chloroform or dichloromethane. The reaction temperature is not specifically limited, but it is usually about −40° C. to about 50° C. The reaction time is several minutes to about 24 hours.

The compound obtained in the 1st to 5th processes can be separated and purified by per se known methods, e.g. concentration, concentration under reduced pressure, distillation under reduced pressure, pH adjustment, solvent transformation, solvent extraction, crystallization, recrystallization or/and chromatography.

The compound (XI) can also be produced easily by the following methods which are known or known per se:

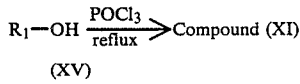 (1)

(XV)

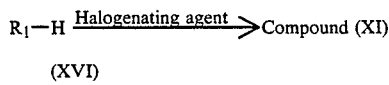 (2)

(XVI)

The compound (XIV) can also be produced easily by the following methods which is known or known per se:

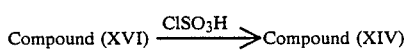

The compounds (IX) and (XV) can be produced easily by the method described in [Advances in Heterocyclic Chemistry, Vol. 6, p. 347, edited by A. R. Katritzky and A. J. Boulton, Academic Press, New York and London, 1966,] or the similar methods.

The compound of the formula (IV) can be produced easily by the methods shown in the following equation, or the methods described in Japanese Published Unexamined Patent Application No. 143686/1976, or Tetrahedron, Vol. 29, p. 691 (1973) etc., or the similar methods.

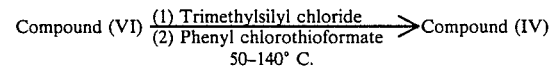

Sulfonyl isothicanates of the formula (V) can be produced easily by the methods described in Angewandte Chemie, International Edition, Vol. 1, p. 553 (1962) and Vol. 4, p. 430 (1965), or the similar methods. The compounds of the formula (VI) can be produced by per se known methods.

The present invention is hereinafter described by Examples in more detail. However, the present invention is not limited to the Examples.

The symbols used in Reference Examples and Examples have the following meaning.

s: singlet d: doublet t: triplet q: quartet m: multiplet

The numeral values for mixture solvents used as eluents in the column chromatography mean the ratios by volume of each solvent mixed.

REFERENCE EXAMPLE 1

Methyl 5-chloro-1,3-dimethylpyrazole-4-carboxylate (Compound A)

6.0 g of methyl 5-amino-1,3-dimethylpyrazole-4carboxylate is dissolved in a mixture of 12 ml of concentrated hydrochloric acid, 12 ml of acetic acid and 7 ml of phosphoric acid, followed by cooling to $-4°$ C. to $-5°$ C. To the mixture is added dropwise a solution of 2.5 g of sodium nitrite in 6 ml of water for 40 minutes to yield a diazonium salt solution (diazotization). Separately, while cooling at 3° C. to 5° C., a solution of 4.0 g of sodium bisulfite in 8.5 g of water is added dropwise to 35 ml of concentrated hydrochloric acid, followed by adding 0.9 g of copper sulfate, pentahydrate. To this mixture are added the diazonium salt solution as prepared above and a solution of 4.0 g of sodium bisulfite in 8.5 ml of water at the same time at 0° C. to 3° C.

The mixture is stirred at the same temperature for 1 hour, and poured into 350 ml of ice water, and extracted with chloroform. The extract is washed with a saturated aqueous sodium chloride solution, a saturated aqueous sodium bicarbonate solution, and then a saturated aqueous sodium chloride solution, in that order, and then dried over anhydrous sodium sulfate. Evaporation of chloroform yields 6.7 g of a yellow-orange oil. This product is distilled under reduced pressure to yield 5.8 g of colorless oil of the title compound.

Yield: 86.7%. bp. 85 to 89° C./0.2 to 0.3 mmHg

IR $\nu$ (liquid film) $cm^{-1}$: 1715, 1525, 1297, 1255, 1112, 1085, 778

Table 1 shows the compounds obtained according to the same procedure as in Reference Example 1 by using different kinds of copper catalysts. Table 2 shows the physico-chemical constants of the obtained compounds (Compounds B to E).

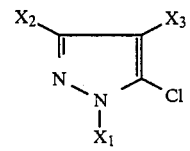

TABLE 1

| Compound No. | $X_1$ | $X_2$ | $X_3$ | Type of Copper Catalyst | Yield (%) |
|---|---|---|---|---|---|
| A | $CH_3$ | $CH_3$ | $COOCH_3$ | CuCl | 85.8 |
| B | $CH_3$ | $CH_3$ | $COOC_2H_5$ | $CuSO_4.5H_2O$ | 88.2 |
|  | $CH_3$ | $CH_3$ | $COOC_2H_5$ | CuCl | 89.6 |
|  | $CH_3$ | $CH_3$ | $COOC_2H_5$ | CuCl | 80.5* |
| C | $CH_3$ | H | $COOC_2H_5$ | CuCl | 79.3 |
| D | $(CH_3)_2CH$ | $CH_3$ | $COOCH_3$ | CuCl | 66.9 |
| E | $(CH_3)_2CH$ | H | $COOCH_3$ | CuCl | 77.1 |

*The starting pyrazole compound is subjected to diazotization after dissolving in a mixture of concentrated hydrochloric acid and water (1:8 by volume).

TABLE 2

| Compound No. | bp. (mp.) | IR $\nu(cm^{-1})$ |
|---|---|---|
| B | 97 to 98° C./0.3 mmHg (38.5 to 39° C.) | (Liquid film) 1708, 1528, 1295, 1242, 1122, 1085, 778 |
| C | 80 to 82° C./0.2 mmHg | (Liquid film) 1715, 1540, 1408, 1225, 1042, 772 |
| D | (60 to 61° C.) | (Nujol) 1717, 1521, 1103, 1289, 1231, 774 |
| E | — | (Liquid film) 1720, 1540, 1247, 1220 |

REFERENCE EXAMPLE 2

Ethyl 5-chloro-1-methylpyrazole-4-carboxylate (Compound C)

23.7 g of ethyl 5-amino-1-methylpyrazole-4-carboxylate is dissolved in a mixture of 50 ml of concentrated hydrochloric acid, 34 ml of acetic acid and 28 ml of phosphoric acid. A solution of 10 g of sodium nitrite in 25 ml of water is added dropwise to the solution while cooling at $-4°$ C. to $-6°$ C. and stirring over a period of 35 minutes to prepare the diazonium salt solution. While cooling at 3° C. to 4° C., the diazonium salt solution is added dropwise to 140 ml of concentrated hydrochloric acid containing 13.9 g of cuprous chloride over a period of 45 minutes. The mixture is stirred at the same temperature for 1 hour, poured into 2l of ice water, and extracted with ethyl acetate. The extract is washed with a saturated aqueous sodium chloride solution, a saturated aqueous sodium bicarbonate solution and a saturated sodium chloride solution in that order, and dried over anhydrous sodium sulfate. Ethyl acetate is evaporated under reduced pressure, and the residue is purified by silica gel column chromatography (eluent, ethyl acetate:toluene=1:1) to give 11.7 g of the titled compound. Yield 44.3%.

REFERENCE EXAMPLE 3

Ethyl 5-chloro-1,3-dimethylpyrazole-4-carboxylate (Compound B)

From 9.2 g of ethyl 5-amino-1,3-dimethylpyrazole-4carboxylate according to the same procedure as that in Reference Example 2, 6.5 g of the title compound is obtained. Yield: 64.4%.

REFERENCE EXAMPLE 4

Methyl 5-chloro-1-methylpyrazole-4-carboxylate 12.1 g of methyl 5-amino-1-methylpyrazole-4-carboxylate is dissolved in a mixture of 28 ml of concentrated hydrochloric acid, 18 ml of acetic acid and 15.6 ml of phosphoric acid. While cooling at $-5°$ C. to $-7°$ C. and stirring, a solution of 5.5 g of sodium nitrite in 7 ml of water is added dropwise to the mixture over a period of 35 minutes to prepare the diazonium salt solution. Separately, to 95 ml of acetic acid saturated with sulfurous acid gas at 0° C. to 3° C., is added 1.6 g of cuprous chloride. To this solution is added dropwise the diazonium salt solution prepared previously over a period of 30 minutes. The reaction mixture is stirred at 0° C. to 4° C. for 2 hours, and then the reaction mixture is poured into 500 ml of water, and extracted with ether. The extract is washed with a saturated aqueous sodium chloride solution, a saturated aqueous sodium bicarbonate solution and a saturated aqueous sodium chloride solution in that order, and dried over anhydrous sodium sulfate. Ether is distilled off to yield 11.6 g of a yellow oil. After the oil is dissolved in hot water, the solution is cooled. Colorless needle crystals separate. The crystals are filtered and dried to yield 11.2 g of the title compound Yield 82.3%.
mp. 69 to 70° C.
IR $\nu$ (nujol) cm$^{-1}$: 1720, 1540, 1227, 1042, 772

REFERENCE EXAMPLE 5

Ethyl 5-benzylthio-1,3-dimethylpyrazole-4-carboxylate 2.3 g of 60% w/w sodium hydride in oil is washed with n-pentane, followed by adding 30 ml of DMF. To the mixture is added 7.2 g of benzylmercaptan while cooling below 10° C., followed by adding a solution of 11.7 g of ethyl 5-chloro-1,3-dimethylpyrazole-4-carboxylate (Compound B) in 10 ml of DMF over a period of 50 minutes while cooling at 0° C. to 8° C. The reaction mixture is stirred at the same temperature for 1 hour and then at room temperature for 30 minutes, and poured into 300 ml of water. The precipitating crystals are collected by filtration, washed with water, and dried to give 15.7 g of the title compound. mp. 51°to 53° C.

This compound is recrystallized from n-hexane to yield colorless crystals showing a melting point of 57°to 58° C.
IR $\nu$ (nujol) cm$^{-1}$: 1700, 1505, 1250, 1130

REFERENCE EXAMPLE 6

Ethyl 5-chlorosulfonyl-1,3-dimethylpyrazole-4-carboxylate 31.5 g of ethyl 5-benzylthio-1,3-dimethylpyrazole-4carboxylate obtained in Reference Example 5 is dissolved in 200 ml of acetic acid, followed by adding 125 ml of water. While cooling at 1° C. to 4° C. and stirring, chlorine gas is bubbled into the mixture over a period of 50 minutes. The reaction mixture is stirred at 0° C. for 40 minutes, and poured into 1l of ice water. The reaction mixture is extracted with ethyl acetate, washed with a saturated aqueous sodium chloride solution, and dried over anhydrous magnesium sulfate. Ethyl acetate is evaporated off and the residue is distilled under reduced pressure to give 26.4 g of the title compound, showing a boiling point of 115 to 119° C./0.25 to 0.3 mmHg.
IR $\nu$ (liquid film) cm$^{-1}$: 1724, 1392, 1255, 1190, 1115

REFERENCE EXAMPLE 7

Ethyl 5-aminosulfonyl-1,3-dimethylpyrazole-4-carboxylate 4.6 g of ethyl 5-chlorosulfonyl-1,3-dimethylpyrazole-4-carboxylate is dissolved in 8 ml of THF, and the solution is added dropwise to 25 ml of ammonia water at 5° C. to 7° C. The reaction mixture is stirred at the same temperature for 1 hour, and then concentrated to dryness under reduced pressure. To the residue is added ethyl acetate, followed by filtration to remove impurities, and the filtrate is concentrated under reduced pressure. The residue is diluted with n-hexane, and then cooled with ice to give crystals. The crystals are filtered and dried to yield 3.6 g of the title compound. mp. 112° to 113° C.
IR $\nu$ (nujol) cm$^{-1}$: 3350, 3240, 1690, 1513, 1355

REFERENCE EXAMPLE 8

5-Benzylthio-1,3-dimethylpyrazole-4-carboxylic acid

A mixture of 100 ml of ethanol, 7.8 g of potassium hydroxide and 35.0 g of ethyl 5-benzylthio-1,3-dimethyl-pyrazole-4-carboxylate obtained in Reference Example 5 is refluxed while stirring for 5 hours. After evaporating off ethanol, dichloromethane is added to the residue, and the resulting solution is extracted with water. After acidifying the aqueous solution to pH 2 with diluted hydrochloric acid, extracted with dichloromethane, and then dried over anhydrous sodium sulfate. Evaporating off dichloromethane yields 27.7 g of the title compound.
NMR(d$_6$-DMSO)$\delta$ ppm: 2.30 (3H, s), 3.40 (3H, s), 4.12 (2H, s), 7.00 to 7.40 (5H, m)

REFERENCE EXAMPLE 9

Isopropyl 5-benzylthio-1,3-dimethylpyrazole-4-carboxylate

A mixture of 27.7 g of 5-benzylthio-1,3dimethyl-pyrazole-4-carboxylic acid obtained in Reference Example 8, 150 ml of thionyl chloride and 1.5 ml DMF is refluxed for 5 hours. The mixture is concentrated under reduced pressure, and the residue is dissolved in 15 ml of dichloromethane, and the dichloromethane solution is added dropwise to 75 ml of isopropanol at 10° C. After stirring for 4 hours, the reaction mixture is concentrated under reduced pressure, and then purified by silica gel column chromatography (eluent, hexane:ethyl acetate =5:1). 18.3 g of the title compound is obtained as an oil.

NMR(CDCl$_3$)δ ppm: 1.35 (3H, s), 1.45 (3H, s), 2.43 (3H, s), 3.49 (3H, s), 4.08 (2H, s),
5.29 (1H m), 6.90 to 7.30 (5H, m)

REFERENCE EXAMPLE 10

Isopropyl 5-aminosulfonyl-1,3-dimethylpyrazole-4carboxylate

From isopropyl 5-benzylthio-1,3-dimethylpyrazole-4carboxylate obtained in Reference Example 9 according to the same procedures as those in Reference Examples 6 and 7, the title compound is obtained. mp. 120° to 122° C.

NMR(CDCl$_3$)δ ppm: 1.32 (3H, s), 1.43 (3H, s), 2.40 (3H, s), 4.10 (3H, s), 5.25 (1H m), 5.97 (2H, broad s)

REFERENCE EXAMPLE 11 n.Propyl 5-aminosulfonyl-1,3-dimethylpyrazole-4carboxylate

From 5-benzylthio-1,3-dimethylpyrazole-4-carboxylic acid according to the same procedures as those described in Reference Examples 9 and 10, the title compound is obtained as an oil.

NMR(CDCl$_3$)δ ppm: 1.02 (3H, t), 1.72 (2H, m),
2.43 (3H, s), 4.12 (3H, s),
4.29 (2H, t), 6.25 (2H, broad s)

REFERENCE EXAMPLE 12 tert-Butyl 5-aminosulfonyl-1,3-dimethylpyrazole-4carboxylate

From 5-benzylthio-1,3-dimethylpyrazole-4-carboxylic acid obtained in Reference Example 8 according to the same procedures as those in Reference Examples 9 and 10 the title compound is obtained as an oil.

NMR(CDCl3)δ ppm: 1.60 (9H, s), 2.40 (3H, s), 4.10 (3H, s), 6.40 (2H, s)

REFERENCE EXAMPLE 13 n-Butyl 5-aminosulfonyl-1,3-dimethylpyrazole-4carboxylate

From 5-benzylthio-1,3-dimethylpyrazole-4-carboxylic acid obtained in Reference Example 8 according to the same procedures as those in Reference Examples 9 and 10, the oily title compound is obtained NMR(CDCl$_3$)δ ppm: 0.90 to 1.90 (7H, m), 2.40 (3H, s) 4.10 (3H, s), 4.30 (2H, s), 6.35 (2H, s)

REFERENCE EXAMPLE 14

Methyl 5-aminosulfonyl-1-isopropyl-3-methylpyrazole-4-carboxylate

From methyl 5-chloro-1-isopropyl-3-methylpyrazole-4carboxylate (Compound D) according to the same procedures as those in Reference Examples 5 to 7, the title compound is obtained.

IR ν(nujol)cm$^{-1}$: 3370, 3270, 1698, 1450, 1112

REFERENCE EXAMPLE 15

Ethyl 5-aminosulfonyl-1-isopropyl-3-methylpyrazole-4-carboxylate

From methyl 5-chloro-1-isopropyl-3-methylpyrazole-4carboxylate (Compound D) according to the same procedures as those in Reference Examples 8 to 10, the title compound is obtained.

IR ν(nujol)cm$^{-1}$ 3330, 3250, 1690, 1372, 1111

REFERENCE EXAMPLE 16

2-Isothiocyanato-4-methoxy-6-methylpyrimidine

To 30 ml of toluene is added 4.2 g of 4-methoxy-6-methyl2-trimethylsilylaminopyrimidine and 3.5 g of phenyl chlorothionocarbonate, and the mixture is stirred for 5.5 hours while heating at about 80° C. After cooling the reaction mixture to room temperature, the precipitates are removed by filtration, and the filtrate is concentrated under reduced pressure. The residue is purified by silica gel column chromatography (eluent, ethyl acetate:toluene =1:3) to yield 2.3 g of the title compound.

mp. 54 to 55° C.

IR ν(nujol)cm$^{-1}$: 1990, 1595, 1560, 1350, 1200, 1045

REFERENCE EXAMPLE 17

Phenyl N-(4,6-dimethoxypyrimidin-2-yl)thionocarbamate

To 10 ml of THF is added 1.0 g of 2-amino-4,6-dimethoxypyrimidine. To the mixture is added dropwise 0.82 g of phenyl chlorothionocarbonate over a period of 5 minutes while stirring at room temperature, followed by reflux for 7 hours. After cooling the reaction mixture to room temperature, insoluble matter is filtered out, and the filtrate is concentrated under reduced pressure. The residue is purified by silica gel column chromatography (eluent, chloroform) to yield 0.1 g of the title compound.

mp. 114° C.

IR ν(nujol)cm$^{-1}$:3200, 1605, 1530, 1325, 1195

REFERENCE EXAMPLE 18

4,6-Dimethoxy-2-isothiocyanatopyrimidine

To 300 ml of acetonitrile are added 45.0 g of 4,6-dimethoxy-2-trimethylsilylaminopyrimidine and 35.0 g of phenyl chlorothionocarbonate, and the mixture is refluxed for 10 hours. The reaction mixture is concentrated under reduced pressure to remove acetonitrile, and 300 ml of toluene is added to the residue. Insoluble matters are removed by filtration and the filtrate is concentrated under reduced pressure, and the residue is purified by silica gel column chromatography (eluent, ethyl acetate:hexane=1:1).

From the primary eluate 17.0 g of 4,6-dimethoxy-2isothiocyanatopyrimidine is obtained.

mp. 85° to 86° C.

IR ν(liquid film)cm$^{-1}$:1995

From the secondary eluate, 3.5 g of 2-[N,N-bis(-phenoxythiocarbonyl)amino]-4,6-dimethoxypyrimidine is obtained.

mp. 127 to 128° C.

IR ν(nujol)cm$^{-1}$:1600, 1295, 1190

REFERENCE EXAMPLE 19

4,6-Dimethyl-2-isothiocyanatopyrimidine

From 4,6-dimethyl-2-trimethylsilylaminopyrimidine and phenyl chlorothionocarbonate according to the same procedure as that in Reference Example 18, a light yellow oil of the title compound is obtained.

bp. 117° to 118° C/2 mmHg
IR $\nu$(liquid film)cm$^{-1}$:1995

REFERENCE EXAMPLE 20

4-Methoxy-6-methyl-2-isothiocyanato-1,3,5-triazine

To 50 ml of xylene are added 15.0 g of 4-methoxy-6-methyl-2-trimethylsilylamino-1,3,5-triazine and 12.2 g of phenyl chlorothionocarbonate. The mixture is stirred at about 140° C. for 6.5 hours. After cooling the reaction mixture to room temperature, insoluble matters are filtered, and the filtrate is concentrated under reduced pressure. The residue is purified by silica gel column chromatography (eluent, ethyl acetate:toluene=1:3) to yield 3.0 g of the title compound as an oil.

IR $\nu$(liquid film)cm$^{-1}$:1970

REFERENCE EXAMPLE 21

4,6-Dimethyl-2-isothiocyanate-1,3,5-triazine

From 4,6-dimethyl-2-trimethylsilylamino-1,3,5triazine and phenyl chlorothionocarbonate according to the same procedure as that in Reference Example 20, a pale yellow oil of the title compound.

IR $\nu$(liquid film)cm$^{-1}$: 1960

REFERENCE EXAMPLE 22

N-(1,3-Dimethyl-4-methoxycarbonyl-5-pyrazolesulfonyl)-N'-(4,6-dimethoxy-2-pyrimidinyl)thiourea (Compound a)

To 150 ml of acetone are added 6.4 g of methyl 5-aminosulfonyl-1,3-dimethylpyrazole-4-carboxylate and 5.6 g of 4,6-dimethoxy-2-isothiocyanatopyrimidine obtained in Reference Example 18, and the mixture is stirred at 43° C. to 45° C. for 12 hours.

The reaction mixture is cooled with ice, and the precipitating crystals are collected by filtration. After suspending the obtained crystals in 300 ml of water, the mixture is adjusted to pH 2 with hydrochloric acid. The separating crystals are filtered, washed with water, and dried to give 9.9 g of crystals. Recrystallization from acetone yields 8.4 g of the title compound.

mp. 149° to 150° C.
IR $\nu$(nujol)cm$^{-1}$:3180, 1720, 1660, 1370, 1200, 1170, 1185

REFERENCE EXAMPLE 23

N-(1,3-Dimethyl-4-ethoxycarbonyl-5-pyrazolesulfonyl)-N'-(4-methoxy-6-methyl-2-pyrimidinyl)thiourea (Compound b)

1.96 g of ethyl 5-aminosulfonyl-1,3-dimethylpyrazole-4-carboxylate and 1.44 g of 2-isothiocyanato-4-methoxy-6-methylpyrimidine obtained in Reference Example 15 are dissolved in 30 ml of acetonitrile. To the solution is added dropwise 1.21 g of DBU while stirring and cooling with ice, followed by stirring at room temperature for 5 hours. The reaction mixture is poured into 150 ml of water, followed by adjusting the mixture to pH 2 with hydrochloric acid. The separating crystals are filtered washed with water, and dried to yield crystals. Recrystallization from acetone yields 0.25 g of the title compound as colorless crystals.

mp. 157° to 158° C.
IR $\nu$(nujol)cm$^{-1}$: 3170, 1708, 1612, 1362, 1255, 1195, 1178
NMR(CDCl$_3$)$\delta$ppm: 1.27 (3H, t), 2.40 (3H, s), 2.52 (3H, s), 4.02 (3H, s), 4.21 (2H, q), 4.29 (3H, s), 6.37 (1H s), 8.82 (1H broad s)

REFERENCE EXAMPLE 24

N-(1,3-Dixethyl-4-ethoxycarbonyl-5-pyrazolesulfonyl)-N'-(4,6-dimethoxy-2-pyrimidinyl)thiourea (Compound c)

A mixture of 1.5 g of ethyl 5-aminosulfonyl1,3-dimethylpyrazole-4-carboxylate, 2.6 g of 2-[N,N-bis(phenoxythiocarbonyl)amino ]-4,6-dimethoxypyrimidine, 0.8 g of anhydrous potassium carbonate and 35 ml of acetone is refluxed for 4 hours. After cooling the mixture to room temperature, an insoluble matter is filtered off, and the filtrate is concentrated to dryness under reduced pressure. The residue is dissolved in a mixture of ethyl acetate and toluene, and is allowed to stand to yield crystals. The crystals are filtered and dissolved in 50 ml of water. The aqueous solution is adjusted to pH 2 with hydrochloric acid to yield crystals. The crystals are filtered, washed with water, and dried to give 0.4 g of the title compound.

mp. 127° to 128° C.
IR $\nu$(nujol)cm$^{-1}$:1 3200, 1715, 1605, 1528, 1362, 1205, 1192, 1183
NMR(CDCl$_3$)$\delta$ ppm:1.28 (3H, t), 2.41 (3H, s), 4.02 (6H, s), 4.23 (2H, q), 4.28 (3H, s), 5.85 (1H s), 8.64 (1H broad s)

Table 3 shows the compounds which are produced according to the same procedures as those in Reference Examples 22 to 24.

TABLE 3

| Compound No. | R$_5$ | R$_6$ | R$_7$ | R$_2$ | R$_3$ | Z | mp. (°C.) | |
|---|---|---|---|---|---|---|---|---|
| d | Me | H | COOMe | OMe | OMe | CH | 143 to 144 | |
| e | Me | H | COOEt | OMe | OMe | CH | 125 to 126 (dec.) | |
| f | Me | H | COOEt | Me | OMe | CH | 158 to 159 | mono potassium |

TABLE 3-continued

[Structure: pyrazole ring with R6, R7, R5 (on N), linked via SO2NH-C(=S)-NH- to a heterocycle with R2, R3, Z, N=]

| Compound No. | R5 | R6 | R7 | R2 | R3 | Z | mp. (°C.) | |
|---|---|---|---|---|---|---|---|---|
| g | Me | Me | COOMe | Me | OMe | CH | 173 to 174 | salt |
| h | Me | Me | COOEt | Me | Me | CH | 127 to 128 | |
| i | Me | Me | COOEt | OMe | OMe | N | 179 to 181 | mono potassium salt |
| j | Me | Me | COOPr(n) | OMe | OMe | CH | >250 | mono potassium salt |
| k | Me | Me | COOPr(i) | OMe | OMe | CH | 122 to 124 (dec.) | mono potassium salt |
| l | Me | Me | COOBu(n) | OMe | OMe | CH | 142 to 144 | |
| m | Me | Me | COOBu(t) | OMe | OMe | CH | 165 to 166.5 | |
| n | Me | Me | CON(Me)2 | OMe | OMe | CH | 152 to 154 | |
| o | Pr(i) | Me | COOMe | OMe | OMe | CH | 154 to 157 | |
| p | Pr(i) | Me | COOMe | OMe | OMe | CH | 150 (dec.) | |
| q | Me | Me | Cl | OMe | OMe | CH | 170 to 172 | |

Me means $CH_3$, Et means $C_2H_5$, Pr means $C_3H_7$,
Bu means $C_4H_9$ (the same in the following Examples)

REFERENCE EXAMPLE 25

5-Benzylthio-4-N,N-dimethylcarbamoyl-1,3-dimethyl-pyrazole

A mixture of 27.7 g 5-benzylthio-1,3-dimethyl- pyrazole-4-carboxylic acid obtained in Reference Example 8, 150 ml of thionyl chloride and 1.5 ml of dimethyl formamide is refluxed for 5 hours. After cooling the reaction mixture, residual thionyl chloride is distilled off under reduced pressure to yield 30.0 g of an oil.

A mixture of 12.0 g of the oil obtained above and 5 ml of dichloromethane is added dropwise to a mixture of 17.2 g of N,N-dimethylamine and 50 ml of dichloromethane while cooling at −60° C. over a period of 1 hour, and then the reaction mixture is stirred at the same temperature for 3 hours. While stirring, the temperature of the reaction mixture is raised to room temperature over a period of 1 hour. The reaction solvent is distilled off, and the residue is purified by silica gel column chromatography (eluent, n-hexane ethyl acetate =1:1) to give 6.5 g of the title compound.

NMR(CDCl3)δ ppm:2.22 (3H, s), 2.94 (3H, broad s), 3.12 (3H, broad s), 3.28 (3H, s), 3.97 (2H, s), 7.00 to 7.40 (5H, m)

REFERENCE EXAMPLE 26

5-Benzylthio-1,3-dimethylpyrazole

A mixture of 2.0 g of ethyl 5-benzylthio-1,3-dimethyl-pyrazole-4-carboxylate, 9 ml of concentrated hydrochloric acid and 6 ml of water is refluxed for 11 hours. The reaction mixture is cooled to room temperature, extracted with chloroform. The extract is washed with a saturated aqueous sodium chloride solution, dried over anhydrous sodium sulfate. Chloroform is evaporated under reduced pressure to yield 1.5 g of the title compound as a colorless oil.

NMR(CDCl3) δ ppm:2 23 (3H, s), 3.51 (3H, s), 3.86 (2H, s), 6.07 (1H s), 7.00 to 7.35 (5H, m)

REFERENCE EXAMPLE 27

4-Chloro-1,3-dimethyl-5-pyrazolesulfonamide (1) To a solution of 1.5 g of 5-benzylthio-1,3dimethylpyrazole obtained in Reference Example 26 in 15 ml of acetic acid is added 5 ml of water. While cooling at 3° C. to 4° C., chlorine gas is bubbled into the mixture over a period of 15 minutes, and then chlorine gas is bubbled into the mixture at 10° C. for 1 hour. The reaction mixture is poured into 100 ml of ice water, and extracted with ether. The extract is dried over anhydrous sodium sulfate, and concentrated under reduced pressure to give 2.0 g of 4-chloro-1,3-dimethyl-5pyrazolesulfonyl chloride as a yellow oil.

NMR(CDCl3)δ ppm:2.29 (3H, s), 4.15 (3H, s)

(2) 2.0 g of 4-chloro-1,3-dimethyl-5-pyrazolesulfonyl chloride obtained in above (1) is dissolved in 8 ml of THF, and to 25 ml of ammonia water is added dropwise to the solution at 8° C. to 10° C. over a period of 10 minutes. After stirring at the same temperature for 1 hour, the solution is concentrated to dryness under reduced pressure, and to the residue is added 30 ml of ethyl acetate. After removing insoluble matter by filtration, the filtrate is concentrated, and purified by silica gel column chromatography (eluent, ethyl acetate:-toluene=2:1) to give 0.45 g of the title compound.

mp. 132° to 134° C.

IR ν(nujol)cm⁻¹:3350, 3210, 1545, 1358, 1345, 1180, 1132, 640, 610

REFERENCE EXAMPLE 28

Ethyl 2-acetyl-3,3-bis(methylthio)acrylate

In 100 ml of dimethyl sulfoxide is dissolved 50.0 g of ethyl acetoacetate. To the solution is added at room temperature 53.1 g of potassium carbonate, and the mixture is stirred for 30 minutes. To the resultant is added, while keeping the inner temperature at 10° C., 29.3 g of carbon disulfide dropwise over a period of 30 minutes, followed by stirring at 10° C. for one hour. To the mixture is further added 120.0g of methyl iodide dropwise at the same temperature over a period of 30 minutes, which is stirred at the same temperature for one hour. The inner temperature is reverted to room temperature, then the reaction mixture is stirred for one hour, poured into 200 ml of ice water, and extracted with dichloromethane. The extract is washed with water, dried and concentrated to give 66.0 g of the title compound as a light brown oil.

NMR(CDCl₃)δ ppm:1.35(3H, t), 2.38(3H, s), 2.45(6H, s), 4.30(2H, q)

REFERENCE EXAMPLE 29

Ethyl 2-acetyl-3,3-(benzylthio)acrylate

In 100 m( of dimethyl sulfoxide is dissolved 35.0 g of ethyl acetoacetate. To the solution is added at room temperature 37.2 g of potassium carbonate, and the mixture is stirred for 30 minutes. To the resultant is added dropwise 20.5 g of carbon disulfide over a period of 30 minutes while keeping the inner temperature at 10° C., followed by stirring at 10° C. for one hour. To the mixture is added dropwise 92.0 g of benzyl chloride at 10° C. over a period of 30 minutes. The whole mixture is stirred at the same temperature for one hour then at room temperature for two hours. The reaction mixture is poured into 200 ml of ice water, and resulting crystals are collected by filtration, washed with water and recrystallized from ethanol to give 69.6 g of the title compound as crystals, m.p. 81 5 to 82.0° C. NMR(CDCl₃)δ ppm:1.25(3H, t), 2.14(3H, s), 4.08(4H, s),
4.23(2H, q), 7.29(10H, s)

REFERENCE EXAMPLE 30

1,3-Dimethyl-4-ethoxycarbonyl-5-methylthiopyrazole

In 50 ml of acetonitrile is dissolved 7.5 g of ethyl 2-acetyl-3,3-bis(methylthio)acrylate. To the solution is added dropwise, while stirring at room temperature (15° C.), 1.8 g of methyl hydrazine over a period of 10 minutes, followed by heating for 7 hours under reflux. After completion of the reaction, the solvent is distilled off under reduced pressure. The residue is purified by means of silica gel column chromatography (eluent, n-hexane:ethyl acetate =4/1 to 2/1) to give 4.1 g of the title compound as an oil.

NMR(CDCl₃)δ ppm:1.38(3H, t), 2.43(6H, s), 3.90(3H, s), 4.35(2H, q)

Elemental analysis for C₉H₁₄N₂O₂S: Calcd. (%) C, 50.45; H, 6.59; N, 13.07 Found (%) C, 50.44; H, 6.58; N, 13.06

REFERENCE EXAMPLE 31

1,3-Dimethyl-4-ethoxycarbonyl-5-benzylthiopyrazole

In 60 ml of acetonitrile is dissolved 10.0 g of ethyl 2-acetyl-3,3-bis(benzylthio)acrylate. To the solution is added dropwise, while stirring at room temperature (15° C.), 1.2 g of methyl hydrazine over a period of 10 minutes, followed by heating for 3 hours under reflux. Then, the solvent is distilled off under reduced pressure. The residue is purified by means of silica gel column chromatography (eluent, n-hexane:ethyl acetate=8/1) to give 5.8 g of the title compound as white crystals, m.p. 55° to 56° C.

NMR(CDCl₃)δ ppm:1.42(3H, t), 2.42(3H, s), 3.37(3H, s), 4.07(2H, s), 4.37(2H, q), 7.00 to 7.40 (5H, m) IR ν(nujol)cm⁻¹: 1700, 1508, 700

Elemental analysis for C₁₅H₁₈N₂O₂S:Calcd. (%) C, 62.05; H, 6.25; N, 9.65 Found (%) C, 62.03; H, 6.20; N, 9.64

EXAMPLE 1

5,7-Dimethoxy-2-(1,3-dimethyl-4-methoxycarbonyl-5-pyrazolesulfonyl)imino-2H-1,2,4-thiadiazolo[2,3-a]pyrimidine (Compound No. 1)

To 50 ml of pyridine is added 4.3 g of N-(1,3-dimethyl-4-methoxycarbonyl-5-pyrazolesulfonyl)-N'(4,6-dimethoxy-2-pyrimidinyl)thiourea, and to the mixture is added 1.6 g of bromine while cooling at −6° C. to −8° C. After stirring at the same temperature for 1.5 hours, the reaction mixture is poured into 300 ml of water. The resulting crystals are filtered, washed with water, and dried. Recrystallization from acetonitrile gives 2.8 g of the title compound as colorless crystals Elemental analysis for C₁₄H₁₆N₆O₆S₂ Calcd. (%) C:39.25; H: 3.76; N: 19.61 Found (%) C:39.44; H: 3.77; N: 19.81 mp. 170° to 171° C.

IR ν(nujol)cm⁻¹:1715, 1625, 1465, 1365, 1100, 918, 902

NMR(d₆-DMSO)δ ppm:2.21 (3H, s), 3.72 (3H, s), 4.01 (3H, s), 4.04 (3H, s), 4.22 (3H, s), 6.60 (1H s)

EXAMPLE 2

5,7-Dimethyl-2-(1,3-dimethyl-4-ethoxycarbonyl-5-pyrazolesulfonyl)imino-2H-1,2,4-thiadiazolo[2,3-a]pyrimidine (Compound No. 2)

0.53 g of N-(1,3-dimethyl-4-ethoxycarbonyl-5-pyrazolesulfonyl)-N'-(4,6-dimethyl-2-pyrimidinyl)-thiourea is suspended in 30 ml of methanol, followed by adding dropwise 0.21 g of bromine while stirring at 0° C. The suspension is stirred at the same temperature for 30 minutes and then at room temperature for 30 minutes. Then the precipitating crystals are filtered and washed with methanol. Recrystallization of the crystals from acetonitrile yields 0.26 g of the title compound as colorless crystals.

Elemental analysis for C₁₅H₁₈N₆O₆S₂:Calcd. (%) C:43.89; H:4.42; N:20.47 Found (%) C 44.00; H:4.39; N:20.45 mp 167° to 168° C.

IR ν(nujol)cm⁻¹:1780, 1650, 1465, 1355, 1303, 1100, 913

NMR(d₆-DMSO)δ ppm:1.24 (3H, t), 2.21 (3H, s), 2.59 (3H, s), 2.69 (3H, s), 4.01 (3H, s), 4.22 (2H q) 7.35 (1H s)

EXAMPLE 3

5,7-Dimethoxy-2-(1,3-dimethyl-4-ethoxycarbonyl-5-pyrazolesulfonyl)imino-2H-1,2,4-thiadiazolo[2,3-a]pyrimidine (Compound No. 3)

0.5 g of N-(1,3-dimethyl-4-ethoxycarbonyl-5-pyrazolesulfonyl)-N'-(4,6-dimethyl-2-pyrimidinyl)thiourea is suspended in 20 ml of methanol, followed by adding 0.2 g of N-bromosuccinimide while stirring at −-4° C. to −5° C. The reaction mixture is stirred at the same temperature for 25 minutes. The separating crystals are filtered, and washed with methanol. Recrystallization of the crystals from acetonitrile yields 0.4 g of the title compound as colorless Elemental analysis for $C_{15}H_{18}N_6O_6S_2$:Calcd. (%) C:40.72; H:4.10; N:18.99 Found (%) C:40.83; H:3.96; N:18.93 mp. 157° to 158° C.

IR $\nu$(nujol)cm$^{-1}$:1722, 1635, 1543, 1465, 1365, 1105, 925, 912

NMR($d_6$-DMSO)$\delta$ ppm:1.25 (3H, t), 2.20 (3H, s), 4.00 (3H, s), 4.03 (3H, s), 4.22 (3H, s), 4.23 (2H, q), 6.60 (1H s)

EXAMPLE 4

5,7-Dimethoxy-2-(4-ethoxycarbonyl-1-methyl-5-pyrazolesulfonyl)imino-2H-1,2,4-thiadiazolo[2,3-a]pyrimidine (Compound No. 4)

0 g of potassium salt of N-(4-ethoxycarbonyl-1-methyl-5-pyrazolesulfonyl)-N'-(4,6-dimethoxy-2-pyrimidinyl)thiourea (acetonitrile-solvate product) is dissolved in 20 ml of pyridine, and to the solution is added dropwise 0.37 g of bromine while cooling at −6° C. to −8° C. The reaction mixture is stirred at the same temperature for 2 hours, and poured into 100 ml of ice water. The resulting crystals are filtered, washed with water, and recrystallized from acetonitrile to give 0.5 g of the title compound as colorless crystals.

Elemental analysis for $C_{14}HY_{16}N_6O_6S_2$:Calcd. (%) C: 39.25; H:3.73; N:19.61 Found (%) C:39.36; H:3.71; N:19.67 mp. 152° to 153° C.

IR $\nu$(nujol)cm$^{-1}$:1 1730, 1710, 1630, 1545, 1465, 1362, 1215, 915

NMR($d_6$-DMSO)$\delta$ ppm:1.30 (3H, t), 4.10 (3H, s), 4.18 (3H, s), 4.26 (3H, s), 4.24 (2H, q), 5.91 (1H s), 7.79 (1H s)

Table 4 shows the compounds which are produced by the same procedures as those in Examples 1-4.

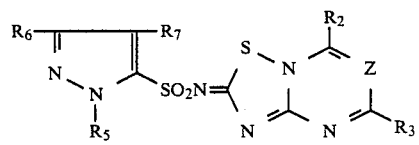

TABLE 4

| Compound No. | $R_5$ | $R_6$ | $R_7$ | $R_2$ | $R_3$ | Z | mp. (°C.) |
|---|---|---|---|---|---|---|---|
| 5 | Me | H | COOMe | OMe | OMe | CH | 167 to 168 |
| 6 | Me | H | COOEt | Me | OMe | CH | 149 to 150 |
| 7 | Me | Me | COOMe | Me | OMe | CH | 172 to 173 |
| 8 | Me | Me | COOEt | Me | OMe | CH | 170 to 171 |
| 9 | Me | Me | COOEt | OMe | OMe | N | 123 to 125 |
| 10 | Me | Me | COOPr(n) | OMe | OMe | CH | 148 to 149.5 |
| 11 | Me | Me | COOPr(i) | OMe | OMe | CH | 161 to 162.5 |
| 12 | Me | Me | COOBu(n) | OMe | OMe | CH | 151 to 153 |
| 13 | Me | Me | COOBu(t) | OMe | OMe | CH | 158 to 159 |
| 14 | Me | Me | CON(Me)$_2$ | OMe | OMe | CH | 131 to 133 |
| 15 | Me | Me | Cl | OMe | OMe | CH | 169 to 170 |

TABLE 4-continued

Formulation Example 1

Emulsifiable concentrates

Emulsifiable concentrates containing the following substances:

| | |
|---|---|
| The compound No. 4 | 2 wt. % |
| Xylene | 75 wt. % |
| Dimethylformamide | 18 wt. % |
| Polyethylene glycol ether (Nonipol 85 ®) | 5 wt. % |

(This composition is diluted with water to appropriate concentration before each application)

Formulation Example 2

Wettable powders

Wettable powders produced by pulverization of a mixture of the following substances:

| | |
|---|---|
| The compound No. 10 | 30 wt. % |
| Sodium ligninsulfonate | 5 wt. % |
| Polyoxyethylene glycol ether (Nonipol 85 ®) | 5 wt. % |
| Clay | 55 wt. % |
| White carbon | 5 wt. % |

(This composition is diluted with water to appropriate concentration before each application)

Formulation Example 3

Granules

Granules produced by kneading a mixture of the following substances with water:

| | |
|---|---|
| The compound No. 3 | 0.2 wt. % |
| Sodium ligninsulfonate | 2 wt. % |
| Bentonite | 57.8 wt. % |
| Talc | 40 wt. % |

Formulation Example 4

Granules

Granules produced by kneading a mixture of the following substances with water:

| | |
|---|---|
| The compound No. 8 | 1.0 wt. % |
| Sodium ligninsulfonate | 5 wt. % |
| Bentonite | 94 wt. % |

Formulation Example 5

Granules

Granules produced by kneading a mixture of the following substances with water:

| | |
|---|---|
| The compound c | 1.0 wt. % |
| Sodium ligninsulfonate | 6.0 wt. % |

-continued

| | |
|---|---|
| Bentonite | 93 wt. % |

TEST EXAMPLE 1

*Echinochloa oryzicola, Cyperus difformis, Monochoria vaginalis, Lindernia procumbens, Rotala indica,* and *Scirpus juncoides* are each seeded in a 1/5000 are Wagner pot containing paddy soil, after which paddy soil containing over-wintering tubers of *Eleocharis aricularis* is scattered in each pot. Both sprouting tubers of *Sagittaria pygmaea* and those of *Cyperus serotinus* are then planted in each pot at the depth of 1 cm and at the soil surface level, respectively. At the same time, young seedlings of rice (variety "Manryo"; raised in separate nursery boxes; 2.0-leaved stagel 12 cm in plant height) are transplanted to each pot and submerged to the depth of 3 cm, immediately after which granules containing the compound of the formula (I) in the ratio of 0.2% by weight, produced according to the same procedure as that in Formulation Example 3, are applied to each pot under submerged conditions so that 0.5 g or 1.0 g of the effective ingredient [the compound (I)]per are is spread. 2.5% Simetryn (granules) as a control is applied so that 2.5 g or 5.0 g of its effective ingredient is spread per are. The herbicidal effect and phytotoxicity by each tested compound are evaluated 21 days after the application.

Herbicidal effect is indicated by the following criteria (also in Test Example shown below).

| Index | Herbicidal Effect | Inhibitory rate (weed-killing rate) % |
|---|---|---|
| 0 | None | 0 |
| 1 | Very weak | 0.1 to 50 |
| 2 | Weak | 50.1 to 70 |
| 3 | Medium | 70.1 to 87.5 |
| 4 | Strong | 87.6 to 99.9 |
| 5 | Maximum | 100 |

Phytoxicity to rice is indicated by the following criteria (also in Test Example 2 shown below).

| Index | Phytotoxicity | Percentage of damage |
|---|---|---|
| 0 | None | 0 |
| 1 | Very small | 0.1 to 12.5 |
| 2 | Small | 12.6 to 30.0 |
| 3 | Medium | 30.1 to 50.0 |
| 4 | Severe | 50.1 to 99.9 |
| 5 | Maximum | 100 |

TABLE 5

| Compound No. | Application Rate (g/are) | Phytotoxicity Rice | Herbicidal Effect | | | | | | | | |
|---|---|---|---|---|---|---|---|---|---|---|---|
| | | | Echinchoria Oryzicola | Cyperus Difformis | Monochoria Vaginalis | Lindernia Procumbens | Rotala Indica | Scirpus Juncoides | Cyperus Serotinus | Eleocharis Aricularis | Sagittaria Pygmaea |
| 1 | 0.5 | 1 | 4 | 4 | 4 | 4 | 4 | 4 | 4 | 4 | 4 |
|   | 1.0 | 2 | 4 | 4 | 4 | 4 | 4 | 4 | 4 | 4 | 4 |
| 3 | 0.5 | 0 | 4 | 4 | 4 | 4 | 4 | 4 | 4 | 4 | 4 |
|   | 1.0 | 0 | 4 | 5 | 5 | 5 | 5 | 4 | 4 | 4 | 4 |
| 4 | 0.5 | 0 | 4 | 4 | 4 | 4 | 4 | 4 | 4 | 4 | 4 |
|   | 1.0 | 0 | 4 | 4 | 4 | 4 | 4 | 4 | 4 | 4 | 4 |
| 5 | 0.5 | 0 | 4 | 4 | 4 | 4 | 4 | 4 | 4 | 4 | 4 |
|   | 1.0 | 0 | 4 | 4 | 4 | 4 | 4 | 4 | 4 | 4 | 4 |
| 6 | 0.5 | 0 | 4 | 4 | 4 | 3 | 4 | 4 | 4 | 4 | 4 |
|   | 1.0 | 0 | 4 | 4 | 4 | 4 | 4 | 4 | 4 | 4 | 4 |
| 7 | 0.5 | 0 | 4 | 4 | 4 | 4 | 4 | 4 | 4 | 4 | 4 |
|   | 1.0 | 1 | 4 | 4 | 4 | 4 | 4 | 4 | 4 | 4 | 4 |
| 8 | 0.5 | 0 | 4 | 4 | 4 | 4 | 4 | 4 | 4 | 4 | 4 |
|   | 1.0 | 0 | 4 | 5 | 5 | 4 | 4 | 4 | 4 | 4 | 4 |
| Control agent: Simetryn | 2.5 | 1 | 1 | 3 | 4 | 4 | 4 | 1 | 1 | 1 | 1 |
|   | 5.0 | 2 | 4 | 4 | 5 | 5 | 5 | 3 | 0 | 2 | 3 |

TEST EXAMPLE 2

*Echinochloa oryzicola, Cyperus difformis, Monochoria vaginalis, Lindernia procumbens, Rotala indica,* and *Scirpus juncoides* are each seeded in a 1/5000 are Wagner pot containing paddy soil, after which paddy soil containing overwintering tubers of *Eleocharis aricularis* is scattered in each pot. Both sprouting tubers of *Sagittaria pygmaea* and those of *Cyperus serotinus* are then planted in each pot at the depth of 1 cm and at the soil surface level, respectively. At the same time, young seedlings of rice (variety: "Manryo"; raised in separate nursery boxes; 2.0-leaved stage; 12 cm in plant height) are transplanted to each pot and submerged to the depth of 3 cm, immediately after which granules containing the compound of the formula (II) in the ratio of 1.0% by weight, produced according to the same procedure as that in Formulation Example 5, are applied to each pot under submerged conditions so that 5 g or 10 g of the effective ingredient [the compound (II)]is spread per are. 2.5% Simetryn granules as a control is applied in the same manner as above. The herbicidal effect and phytotoxicity by each compound are evaluated 21 days after the application.

Table 6 shows the results.

TABLE 6

| Compound No. | Application Rate (g/are) | Phytotoxicity Rice | Herbicidal Effect | | | | | | | | |
|---|---|---|---|---|---|---|---|---|---|---|---|
| | | | Echinchoria Oryzicola | Cyperus Difformis | Monochoria Vaginalis | Lindernia Procumbens | Rotala Indica | Scirpus Juncoides | Cyperus Serotinus | Eleocharis Aricularis | Sagittaria Pygmaea |
| a | 5 | 0 | 4 | 4 | 4 | 3 | 4 | 4 | 4 | 4 | 4 |
|   | 10 | 1 | 4 | 4 | 4 | 4 | 4 | 4 | 4 | 4 | 4 |

TABLE 6-continued

| Compound No. | Application Rate (g/are) | Phyto-toxicity Rice | Herbicidal Effect ||||||||| 
|---|---|---|---|---|---|---|---|---|---|---|---|
| | | | Echin-choria Oryzicola | Cyperus Difformis | Monochoria Vaginalis | Lindernia Procumbens | Rotala Indica | Scirpus Juncoides | Cyperus Serotinus | Eleocharis Aricularis | Sagittaria Pygmaea |
| d | 5 | 0 | 3 | 4 | 4 | 3 | 4 | 4 | 3 | 4 | 4 |
| | 10 | 0 | 4 | 4 | 4 | 3 | 4 | 4 | 4 | 4 | 4 |
| f | 5 | 0 | 3 | 4 | 4 | 3 | 4 | 4 | 3 | 4 | 4 |
| | 10 | 0 | 4 | 4 | 4 | 4 | 4 | 4 | 3 | 4 | 4 |
| Control agent: Simetryn | 5 | 2 | 4 | 4 | 5 | 5 | 5 | 5 | 0 | 2 | 3 |
| | 10 | 3 | 5 | 5 | 5 | 5 | 5 | 4 | 1 | 3 | 4 |

What is claimed is:

1. A compound of the formula

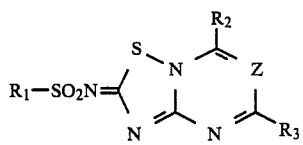

wherein $R_1$ is a pyrazolyl group which is unsubstituted of mono- to tri-substituted by a lower alkyl group, a lower alkenyl group, a lower alkynyl group, a lower alkoxy group, a lower alkenyloxy group, an aryl group of 6 to 12 carbon atoms, an aryloxy group of 6 to 12 carbon atoms, an aralkyl group of 7 to 10 carbon atoms, an aralkyloxy group of 7 to 10 carbon atoms, an acyl group derived from an organic carboxylic acid but excluding carbamoyl, an acyloxy group in which the acyl group is derived from an organic carboxylic acid but excluding carbamoyloxy, a carbamoyl group, a carbamoyloxy group, sulfamoyl, halogen, a carboxy group which may be esterified, or cyano or said pyrazolyl group is mono-substituted by nitro or a group of the formula:

in which $R_4$ is an organic residue and n is an integer of 0, 1 or 2;
$R_2$ and $R_3$ respectively are a lower alkyl group or a lower alkoxy group; and Z is CH.

2. A compound as claimed in claim 1, wherein $R_1$ is a pyrazolyl group which is unsubstituted or is mono- to tri-substituted by a lower alkyl group, a lower alkenyl group, a lower alkynyl group, a lower alkoxy group, an aryl group of 6 to 12 carbon atoms, an aralkyl group of 7 to 10 carbon atoms, an aralkyloxy group of 7 to 10 carbon atoms, a carbamoyl group which may be mono- or di-substituted by a lower alkyl group, halogen, a carboxyl group which may be esterified, or cyano or said pyrazolyl group is mono-substituted by nitro or a group of the formula

wherein $R_4$ is a lower alkyl group; and n is 0, 1 or 2.

3. A herbicidal composition which comprises a herbicidally effective amount of a compound according to claim 1, and a suitable carrier therefor.

4. A compound as claimed in claim 2, wherein the pyrazolyl group is a pyrazol-5-yl group.

5. A compound as claimed in claim 1, wherein $R_1$ is a group of the formula

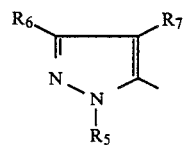

wherein $R_5$ is a lower alkyl group; $R_6$ is hydrogen or a lower alkyl group and $R_7$ is an optionally esterified carboxyl group, halogen, a carbamoyl group which may be mono- or di-substituted by a lower alkyl group.

6. A compound as claimed in claim 5, wherein $R_7$ is carboxyl esterified by a lower alkyl group.

7. A compound as claimed in claim 5, wherein $R_2$ is methyl or methoxy; $R_3$ is methoxy; $R_5$ is methyl; $R_6$ is hydrogen or methyl and $R_7$ is methoxycarbonyl or ethoxycarbonyl.

8. A compound as claimed in claim 1, namely 5,7-dimethoxy-2-(1,3dimethyl-4-ethoxycarbonyl-5-pyrazolesulfonyl)imino-2H-1,2,4-thiadiazolopyrimidine.

9. A compound as claimed in claim 1, namely 5,7-dimethoxy-2-(1-methyl-4-ethoxycarbonyl-5-pyazolesulfonyl) imino-2H-1,2,4-thiadiazolopyrimidine.

* * * * *